United States Patent
Machold et al.

(10) Patent No.: US 12,383,255 B2
(45) Date of Patent: Aug. 12, 2025

(54) SUTURE MANAGEMENT DEVICE AND METHODS

(71) Applicant: MVRx, Inc., San Mateo, CA (US)

(72) Inventors: Timothy R. Machold, Moss Beach, CA (US); David R. Tholfsen, San Leandro, CA (US)

(73) Assignee: MVRx, Inc., San Mateo, CA (US)

( * ) Notice: Subject to any disclaimer, the term of this patent is extended or adjusted under 35 U.S.C. 154(b) by 933 days.

(21) Appl. No.: 17/426,879

(22) PCT Filed: Jan. 30, 2020

(86) PCT No.: PCT/US2020/015810
§ 371 (c)(1),
(2) Date: Jul. 29, 2021

(87) PCT Pub. No.: WO2020/160218
PCT Pub. Date: Aug. 6, 2020

(65) Prior Publication Data
US 2022/0096076 A1     Mar. 31, 2022

Related U.S. Application Data

(60) Provisional application No. 62/799,574, filed on Jan. 31, 2019.

(51) Int. Cl.
*A61B 17/04*     (2006.01)
*A61B 17/00*     (2006.01)
*A61B 17/06*     (2006.01)

(52) U.S. Cl.
CPC ...... *A61B 17/0469* (2013.01); *A61B 17/0057* (2013.01); *A61B 17/0482* (2013.01);
(Continued)

(58) Field of Classification Search
CPC ............ A61B 17/0057; A61B 17/0469; A61B 17/0482; A61B 17/0487; A61B 17/06119;
(Continued)

(56) References Cited

U.S. PATENT DOCUMENTS

| | | |
|---|---|---|
| 6,612,515 B1 | 9/2003 | Tinucci et al. |
| 9,370,368 B2 | 6/2016 | Jayant |

(Continued)

FOREIGN PATENT DOCUMENTS

| | | |
|---|---|---|
| JP | 2008534085 A | 8/2008 |
| JP | 2013534170 A | 9/2013 |

(Continued)

OTHER PUBLICATIONS

EP Partial Search Report in European Application No. 20747875, dated Oct. 10, 2022, 15 pages.
(Continued)

*Primary Examiner* — Robert A Lynch
(74) *Attorney, Agent, or Firm* — DLA Piper LLP (US)

(57) ABSTRACT

Delivery systems, methods and associated devices for management of an elongate element having sections with differing mechanical properties, in particular, for management of a loop of suture-wire element extending proximally from a delivery catheter for deployment of a heart implant. Such management devices can include an inner feature (e.g. outward facing groove or series of tabs) along an inner circle about which a suture can be coiled and an outer feature (e.g. inward facing groove or tabs) to engage and constrain a wire section having increased stiffness within a coil having a larger diameter than the coiled suture. Such devices can be provided separately or can be integrated within a handle of the delivery catheter. Methods of loading suture-wire management devices and utilizing such devices during deployment of an implantable anchor are also described herein.

25 Claims, 28 Drawing Sheets

(52) U.S. Cl.
CPC ............... *A61B 17/0487* (2013.01); *A61B 2017/00623* (2013.01); *A61B 2017/00876* (2013.01); *A61B 2017/0496* (2013.01); *A61B 2017/06142* (2013.01); *A61B 2017/06171* (2013.01)

(58) Field of Classification Search
CPC .... A61B 17/06123; A61B 2017/00623; A61B 2017/00876; A61B 2017/0496; A61B 2017/06142; A61B 2017/06171
See application file for complete search history.

(56) References Cited

U.S. PATENT DOCUMENTS

| | | | |
|---|---|---|---|
| 9,498,206 B2 | 11/2016 | Fung et al. | |
| 9,500,831 B2 | 11/2016 | Haataja | |
| 2004/0087979 A1* | 5/2004 | Field | A61B 17/068 606/148 |
| 2008/0091059 A1 | 4/2008 | Machold et al. | |
| 2010/0318105 A1 | 12/2010 | Jayant | |
| 2011/0046642 A1* | 2/2011 | McClurg | A61B 17/0469 606/139 |
| 2012/0316581 A1* | 12/2012 | Gaynor | A61B 17/0482 606/146 |
| 2013/0144311 A1 | 6/2013 | Fung et al. | |
| 2013/0287359 A1 | 10/2013 | Haataja | |
| 2016/0367240 A1* | 12/2016 | Shelton, IV | A61B 17/06166 |

FOREIGN PATENT DOCUMENTS

| | | |
|---|---|---|
| WO | WO 2012/023983 A1 | 2/2012 |
| WO | WO 2012167797 A1 | 12/2012 |

OTHER PUBLICATIONS

JP Office Action in Japanese Application No. 2021-544908, dated Oct. 12, 2023, 9 pages (with English translation).

* cited by examiner

SUTURE MANAGEMENT DEVICE AND METHODS

CROSS-REFERENCES TO RELATED APPLICATIONS

This application is a 35 USC § 371 National Stage application of International Application No. PCT/US2020/015810 filed Jan. 30, 2020, now pending; which claims the benefit under 35 USC § 119 (e) to U.S. Application Ser. No. 62/799,574 filed Jan. 31, 2019. The disclosure of each of the prior applications is considered part of and is incorporated by reference in the disclosure of this application.

This application is generally related to U.S. Provisional Application Ser. No. 62/541,375 filed on Aug. 4, 2017, entitled "DELIVERY SYSTEM AND METHODS FOR RESHAPING A HEART VALVE ANNULUS, INCLUDING THE USE OF MAGNETIC TOOLS", and U.S. Non-Provisional application Ser. No. 16/056,220 filed on Aug. 6, 2018, entitled "DELIVERY SYSTEM AND METHODS FOR RESHAPING A HEART VALVE ANNULUS, INCLUDING THE USE OF MAGNETIC TOOLS", which are incorporated by reference herein for all purposes.

FIELD OF THE INVENTION

The invention is directed to devices, systems, and methods for managing an elongate element having sections with differing mechanical properties, in particular, a suture-wire element to facilitate deployment of a heart implant having a bridging element.

BACKGROUND OF THE INVENTION

Treatments for mitral valve regurgitation are widely varied. A particularly promising approach entails delivery of an implant having a bridging element across a chamber of the heart such that tensioning of the implant reshapes the heart chamber, thereby improving coaptation of the mitral valve. Some such implants are delivered intravascularly by advancing a suture-wire element, a portion of which includes a bridging element, through the vasculature of the patient from a first vascular access point and exiting through a second vascular access point. While this delivery technique has marked advantages over conventional approaches, it involves use of a relatively long suture-wire element. Managing this element before and during advancement through the vasculature can be cumbersome, particularly since the element must be maintained as sterile and smoothly fed into the vasculature without tangling. Typically, the element is a suture-wire having sections of differing materials, for example, a wire section of a stiff material having compressive strength (e.g. guidewire, needle) and a suture section having reduced compressive strength prone to tangling and catching adjacent objects. Further, having each end of the continuous suture wire element stored side by side in small lumen of long catheter to be deployed one sequentially before the other presents other unique challenges. The different mechanical properties of these differing sections and the preferred deployment scheme present unique challenges that are unmet by conventional suture or guidewire management approaches. Therefore, there is a need for devices and methods that provide improved storage and management of suture-wire elements for deploying an implant. It is desirable for such devices and methods to also maintain sterility of the element and facilitate smooth dispensing when needed.

I. The Anatomy of a Healthy Heart

As can be seen in FIG. 2A, the human heart is a double-sided (left and right side), self-adjusting pump, the parts of which work in unison to propel blood to all parts of the body. The right side of the heart receives poorly oxygenated ("venous") blood from the body from the superior vena cava and inferior vena cava and pumps through the pulmonary artery to the lungs for oxygenation. The left side receives well-oxygenation ("arterial") blood from the lungs through the pulmonary veins and pumps into the aorta for distribution to the body.

The heart has four chambers, two on each side—the right and left atria, and the right and left ventricles. The atriums are the blood-receiving chambers, which pump blood into the ventricles. The ventricles are the blood-discharging chambers. A wall composed of fibrous and muscular parts, called the interatrial septum separates the right and left atriums (see FIGS. 2B-2D). An anatomic landmark on the interatrial septum is an oval, thumbprint sized depression called the oval fossa, or fossa ovalis (FO), shown in FIG. 2C, which is a remnant of the oval foramen and its valve in the fetus and thus is free of any vital structures such as valve structure, blood vessels and conduction pathways. The synchronous pumping actions of the left and right sides of the heart constitute the cardiac cycle. The cycle begins with a period of ventricular relaxation, called ventricular diastole. The cycle ends with a period of ventricular contraction, called ventricular systole 3. The heart has four valves (see FIGS. 2B and 2C) that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

At the beginning of ventricular diastole (i.e., ventricular filling), the aortic and pulmonary valves are closed to prevent back flow from the arteries into the ventricles. Shortly thereafter, the tricuspid and mitral valves open, as shown in FIG. 2B, to allow flow from the atriums into the corresponding ventricles. Shortly after ventricular systole (i.e., ventricular emptying) begins, the tricuspid and mitral valves close, as shown in FIG. 2C—to prevent back flow from the ventricles into the corresponding atriums—and the aortic and pulmonary valves open—to permit discharge of blood into the arteries from the corresponding ventricles.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

As FIGS. 2B-2C show, the anterior (A) portion of the mitral valve annulus is intimate with the non-coronary leaflet of the aortic valve. Notably, the mitral valve annulus is near other critical heart structures, such as the circumflex branch of the left coronary artery (which supplies the left atrium, a variable amount of the left ventricle, and in many people the SA node) and the AV node (which, with the SA node, coordinates the cardiac cycle). In the vicinity of the posterior (P) mitral valve annulus is the coronary sinus and its tributaries. These vessels drain the areas of the heart supplied by the left coronary artery. The coronary sinus and its tributaries receive approximately 85% of coronary venous blood. The coronary sinus empties into the posterior of the right atrium, anterior and inferior to the fossa ovalis, as can be seen FIG. 2C. A tributary of the coronary sinus is called the great cardiac vein, which courses parallel to the majority of the posterior mitral valve annulus, and is superior to the posterior mitral valve annulus by an average distance of about 9.64+/−3.15 millimeters (Yamanouchi, Y, *Pacing and Clinical Electrophysiology* 21(11):2522-6; 1998).

II. Characteristics and Causes of Mitral Valve Dysfunction

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

In a healthy heart (shown in FIGS. 2E-2F), the dimensions of the mitral valve annulus create an anatomic shape and tension such that the leaflets coapt, forming a tight junction, at peak contraction pressures. Where the leaflets coapt at the opposing medial (CM) and lateral (CL) sides of the annulus are called the leaflet commissures. Valve malfunction can result from the chordae tendineae (the chords) becoming stretched, and in some cases tearing. When a chord tears, the result is a leaflet that flails. Also, a normally structured valve may not function properly because of an enlargement of or shape change in the valve annulus. This condition is referred to as a dilation of the annulus and generally results from heart muscle failure. In addition, the valve may be defective at birth or because of an acquired disease. Regardless of the cause, mitral valve dysfunction can occur when the leaflets do not coapt at peak contraction pressures, as shown in FIG. 2G. In such cases, the coaptation line of the two leaflets is not tight at ventricular systole. As a result, an undesired back flow of blood from the left ventricle into the left atrium can occur, commonly known as mitral regurgitation. This has two important consequences. First, blood flowing back into the atrium may cause high atrial pressure and reduce the flow of blood into the left atrium from the lungs. As blood backs up into the pulmonary system, fluid leaks into the lungs and causes pulmonary edema. Second, the blood volume going to the atrium reduces volume of blood going forward into the aorta causing low cardiac output. Excess blood in the atrium over-fills the ventricle during each cardiac cycle and causes volume overload in the left ventricle.

Mitral regurgitation is categorized into two main types, (i) organic or structural and (ii) functional. Organic mitral regurgitation results from a structurally abnormal valve component that causes a valve leaflet to leak during systole. Functional mitral regurgitation results from annulus dilation due to primary congestive heart failure, which is itself generally surgically untreatable, and not due to a cause like severe irreversible ischemia or primary valvular heart disease. Organic mitral regurgitation is seen when a disruption of the seal occurs at the free leading edge of the leaflet due to a ruptured chord or papillary muscle making the leaflet flail; or if the leaflet tissue is redundant, the valves may prolapse the level at which coaptation occurs higher into the atrium with further prolapse opening the valve higher in the atrium during ventricular systole. Functional mitral regurgitation occurs as a result of dilation of heart and mitral annulus secondary to heart failure, most often as a result of coronary artery disease or idiopathic dilated cardiomyopathy. Comparing a healthy annulus in FIG. 2E to an unhealthy annulus in FIG. 2G, the unhealthy annulus is dilated and, in particular, the anterior-to-posterior distance along the minor axis (line P-A) is increased. As a result, the shape and tension defined by the annulus becomes less oval (see FIG. 2E) and more round (see FIG. 2G). This condition is called dilation. When the annulus is dilated, the shape and tension conducive for coaptation at peak contraction pressures progressively deteriorate.

III. Prior Treatment Modalities

It is reported that twenty-five percent of the six million Americans who will have congestive heart failure will have functional mitral regurgitation to some degree. This constitutes the 1.5 million people with functional mitral regurgitation. In the treatment of mitral valve regurgitation, diuretics and/or vasodilators can be used to help reduce the amount of blood flowing back into the left atrium. An intra-aortic balloon counterpulsation device is used if the condition is not stabilized with medications. For chronic or acute mitral valve regurgitation, surgery to repair or replace the mitral valve is often necessary.

By interrupting the cycle of progressive functional mitral regurgitation, it has been shown in surgical patients that survival is increased and in fact forward ejection fraction increases in many patients. Given the significant insult imposed by surgery, surgical repair on these chronically ill patients is associated with high morbidity and mortality rates.

Currently, patient selection criteria for mitral valve surgery are very selective and typically performed only on patients having normal ventricular function, generally good health, a predicted lifespan of greater than 3 to 5 years, NYHA Class III or IV symptoms, and at least Grade 3 regurgitation. Patients that do not meet these requirements, typically older patients in poor health, are not good candidates for surgical procedures, especially open surgical procedures. Such patients benefit greatly from shorter, less invasive surgical procedures that improve valve function, such as any of those described in U.S. application Ser. No. 14/945,722. However, such patients could benefit from further improvements in minimally invasive surgical procedures to deploy such valve treatment and repair implant systems, reducing the complexity of delivery systems and duration of the procedures, as well as consistency, reliability and ease of use.

Thus, there is a need for further improvements that reduce the complexity of such delivery systems and improved methods of delivery that reduce the duration of the procedures, and improve the consistency, reliability and ease of use for the clinician, e.g., in the deployment of heart implants for treatment of mitral valve regurgitation.

BRIEF SUMMARY OF THE INVENTION

The invention is directed to devices, systems, and methods for managing an elongate element having sections with differing mechanical properties, in particular, a suture-wire element to facilitate deployment of a heart implant having a bridging element.

In one aspect, the invention pertains to a suture-wire element management device that is incorporated into a catheter handle. In some embodiments, the integrated catheter handle includes a catheter handle body having a proximal portion and a distal portion, a catheter shaft and a hemostatic port provided in the distal portion, and an enclosure disposed along the proximal portion, the enclosure being configured for storing and managing a loop of excess suture-wire element extending proximally from the hemostatic port. In some embodiments, the enclosure includes an inner groove facing radially outward to facilitate winding of a suture section of the suture-wire element thereon within a coil, and an outer groove facing radially inward to radially constrain a wire section of the suture-wire element in a coil. In some embodiments, the enclosure is defined by a proximal portion of the catheter body that interfaces with a releasable cap. The cap can include a central opening through which the wire sections and suture sections are sequentially dispensed from their respective coils. An interior of the enclosure can include a cylindrical or conical post disposed having a radially extending upper lip of the post that defines the inner groove. The outer groove can be defined by a proximal portion of the catheter body or a portion of the cap. The outer groove can be defined as a rounded triangular recess to facilitate sequential coiling of the wire section. In some embodiments, the enclosure includes a slit extending radially from the central opening for passage of a portion of the suture section to avoid interference or tangling when dispensing excess suture-wire element through the central opening. In some embodiments, the cap having the central opening and slit is rotatable, for example by at least 180°, such that the radial slit aligns with the lengthwise slit of the cap to facilitate release of a last remaining portion of the suture section from the enclosure.

In another asepct, the invention pertains to a catheter system for delivery of a heart implant. In some embodiments, the delivery system includes a first catheter having a proximal and distal end, the first catheter including a first lumen extending therethrough for passage of a guidewire and a magnetic head along a distal portion, the magnetic head having a guide channel defined therein and extending to a side hole adjacent a first magnetic pole; a penetrating wire section of a suture-wire element advanceable through a second lumen aligned with the guide channel of the distal magnetic head, the penetrating wire section having a sharpened distal end to facilitate penetration of tissue; an anchor releasably coupled along a distal portion of the catheter; and a suture section configured to act as a bridging element in the implant, the suture section being attached to the posterior anchor at one end and attached to the penetrating wire section at an opposite end. The system further includes a suture-wire management device configured for managing suture-wire element extending proximally of the first catheter during delivery and deployment of the posterior anchor, typically, a loop of the suture-wire element. The device can include any of the suture-wire management features described herein, and can be provided as a separate device or can be integrated within a handle of the catheter, such as described above.

In another aspect, the suture-management device can be an enclosure defined by a housing. In some embodiments, the device includes a housing having a generally rounded shape; an inner groove surface defined within the enclosure that faces in a radially outward direction for winding of the suture section thereon within a coil; an outer groove surface defined within the enclosure that faces radially inward for constraining a coil of the wire section therein. In some embodiments, the device further includes an opening along an upper surface of the housing for dispensing of the suture-wire element therethrough from within the enclosure. In some embodiments, the housing further includes a slit emanating from the circular opening and extending at least partly along one side of the housing for passage of a portion of the suture section therethrough. In some embodiments, the device can further include a compression band or O-ring fits dimensioned and configured to secure the suture section coil while dispensing the wire needle section through the opening.

In another aspect, the invention pertains to methods of loading a suture-wire element on a suture-wire management device. In particular, methods of loading are described that facilitate deployment of a heart implant device having a bridging element defined by a portion of a suture section of the suture-wire element. Such methods can include: placing the suture section within the device such that a portion of the suture section extends into an enclosure of the device or is secured onto the device; winding the suture section about an inner winding surface of the device within a first coil; and after winding the suture section, winding the needle wire section of increased stiffness about an outer winding surface of the device that constrains the needle wire section within a second coil having a larger diameter than the first coil. In some embodiments, for example for heart implant delivery applications, a portion of the suture section extends under the second coil of the needle wire coil so as to facilitate dispensing of the needle wire section from the second coil before dispensing of the suture section from the first coil. In some embodiments, after winding the wire section within the second coil, a distal end of the wire section is fed through a hemostatic port in a catheter handle of an implant delivery catheter and the wire section is advanced so as to position the distal end at or near the distal end of the delivery catheter.

In another aspect, the suture-wire management device can be defined as a planar member formed of a substantially rigid or semi-rigid material. The planar member can include a first and second series of tabs. In some embodiments, the first set of tabs are disposed along an outer periphery of the planar member and angled radially inward so as to constrain the wire needle section within a first coil, while the second series of tabs are disposed within an inner circle of the planar member and angled radially outward to facilitate winding of the suture section thereon in a second coil, the second coil having a diameter less than that of the first coil. The tabs can be defined in the planar member itself or be provided as separate features attached to the planar member. In some embodiments, the first and second sets of tabs are radially aligned with each other to avoid interference during dispensing of the suture-wire elements from the respective coils. The tabs can be provided on the same side of the planar member or opposite sides. The planar member can further include a slot along an outer periphery for securing the suture section element along or near where the suture section transitions to the wire section.

In yet another aspect, the suture-wire management device can be defined as a sleeve member having a closed distal end and an open proximal end, the sleeve member having a length greater than a length of the loop of suture-wire element, and a retention feature disposed within distally within the sleeve that is configured to be releasably engageable with a folded portion of suture-wire to facilitate controlled movement and release of the suture-wire from the sleeve. Typically, the retention feature is slidably movable along the length of the sleeve and removable through a proximal opening of the sleeve. In some embodiments, the retention feature is a ring through which the excess suture-wire element extends and from which the loop of suture-wire is releasable upon removal of the ring from the sleeve.

While the suture-wire management device is described throughout in regard to management of a suture-wire element to facilitate deployment of a heart implant having a tensioned bridging element, it is understood that these concepts described are applicable to deployment of various other types of implants and further suitable for management of any elongate element having sections with differing mechanical properties.

Other features and advantages of the invention shall be apparent based upon the accompanying description, drawings, and claims.

DETAILED DESCRIPTION OF THE INVENTION

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1A:
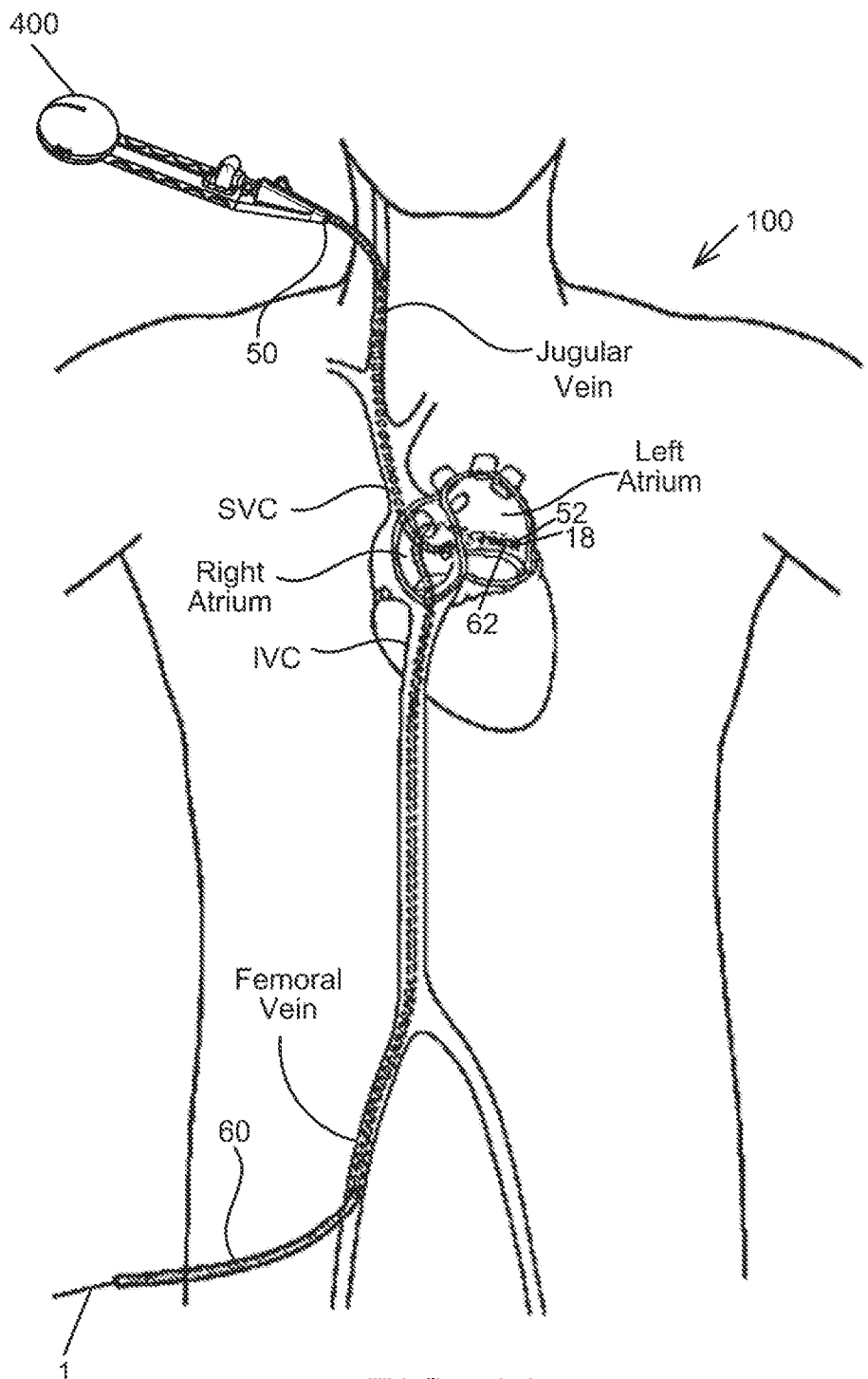
FIG. 1A depicts an overview of a catheter system for intravascular delivery of a heart implant for treatment of mitral regurgitation that includes a delivery catheter handle with integrated suture-wire management, in accordance with embodiments of the invention.
Figure 1B:
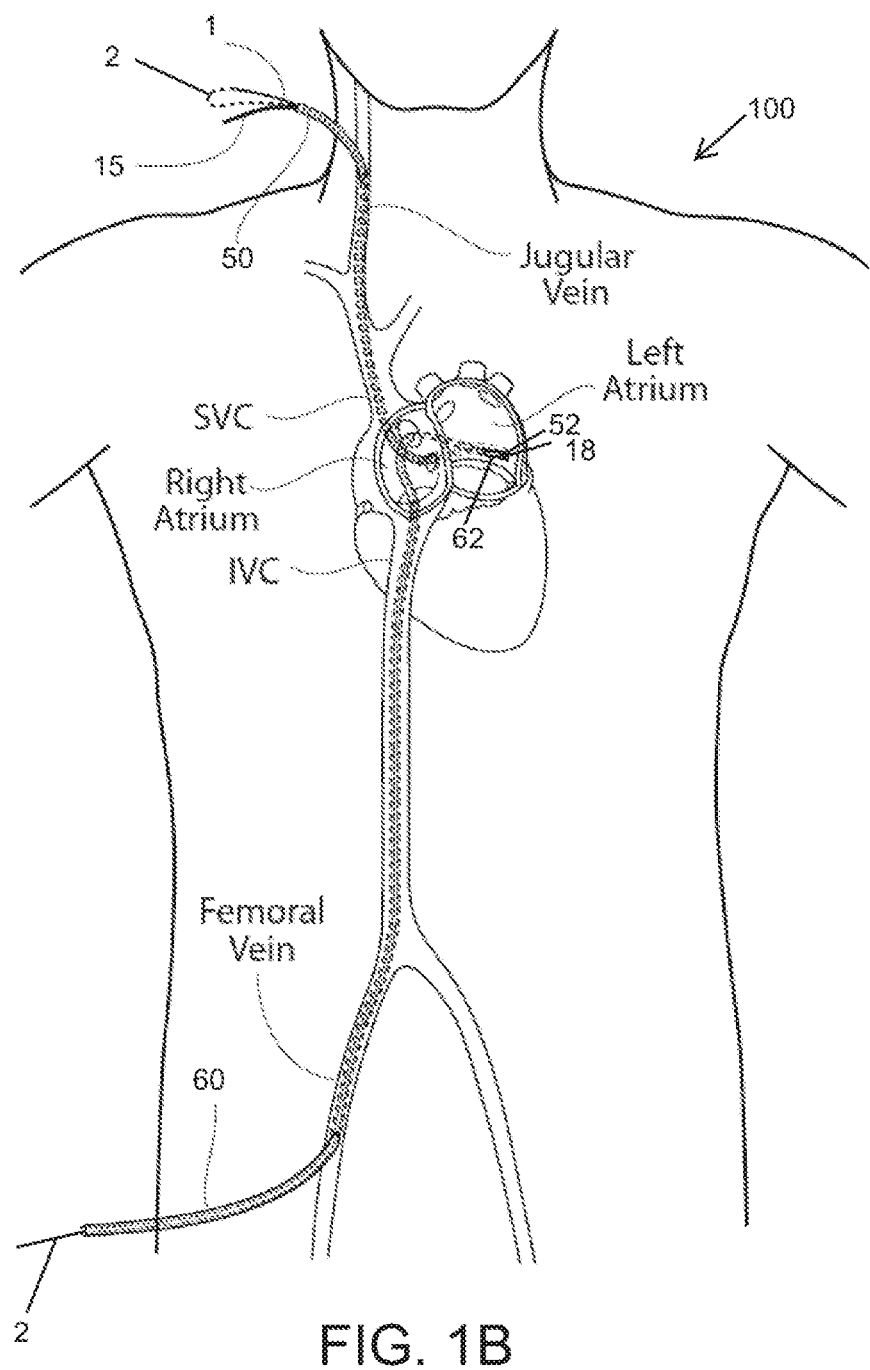
FIG. 1B depicts an overview of a catheter system for intravascular delivery of a heart implant and shows the suture-wire element extending proximally of the delivery catheter, in accordance with embodiments of the invention.

FIG. 1A shows an example embodiment of a catheter-based delivery system 100 in accordance with aspects of the invention. The delivery system utilizes a pair of magnetic catheters that are advanced from separate vascular access points and magnetically coupled across a tissue within the heart. The pair of catheters include a great cardiac vein (GCV) anchor delivery catheter 50 which is introduced from the jugular vein and advanced along a superior vena cava (SVC) approach to the GCV, and a left atrial (LA) catheter 60, which is introduced at the femoral vein and introduced along an inferior vena cava (IVC) approach, across the inter-atrial septum and into the left atrium. Each catheter includes a magnetic head along a distal portion thereof (magnetic head 52 of catheter 50 and magnetic head 62 of catheter 60) such that when magnetically coupled, the catheters provide a stable region to facilitate penetration of a tissue wall between the LA and GCV and subsequent advancement of the puncturing guidewire 1 through the GCV catheter 50 and into the LA catheter 60. Notably, a trailing end of the puncturing wire needle guidewire 1 is attached to one end of a suture bridging element 1 (e.g. suture), the other end of which is attached to posterior anchor 18 disposed on the distal portion of GCV catheter 50. GCV delivery catheter 50 includes a proximal catheter handle 400 with integrated suture-wire management device for storing and managing excess suture-wire during the implant deployment procedures described herein. As can be seen in FIG. 1B, a loop of excess bridging element extends proximally outside of the catheter lumen, which is managed by the suture-wire management device in the catheter handle, as described herein.

Figure 13:
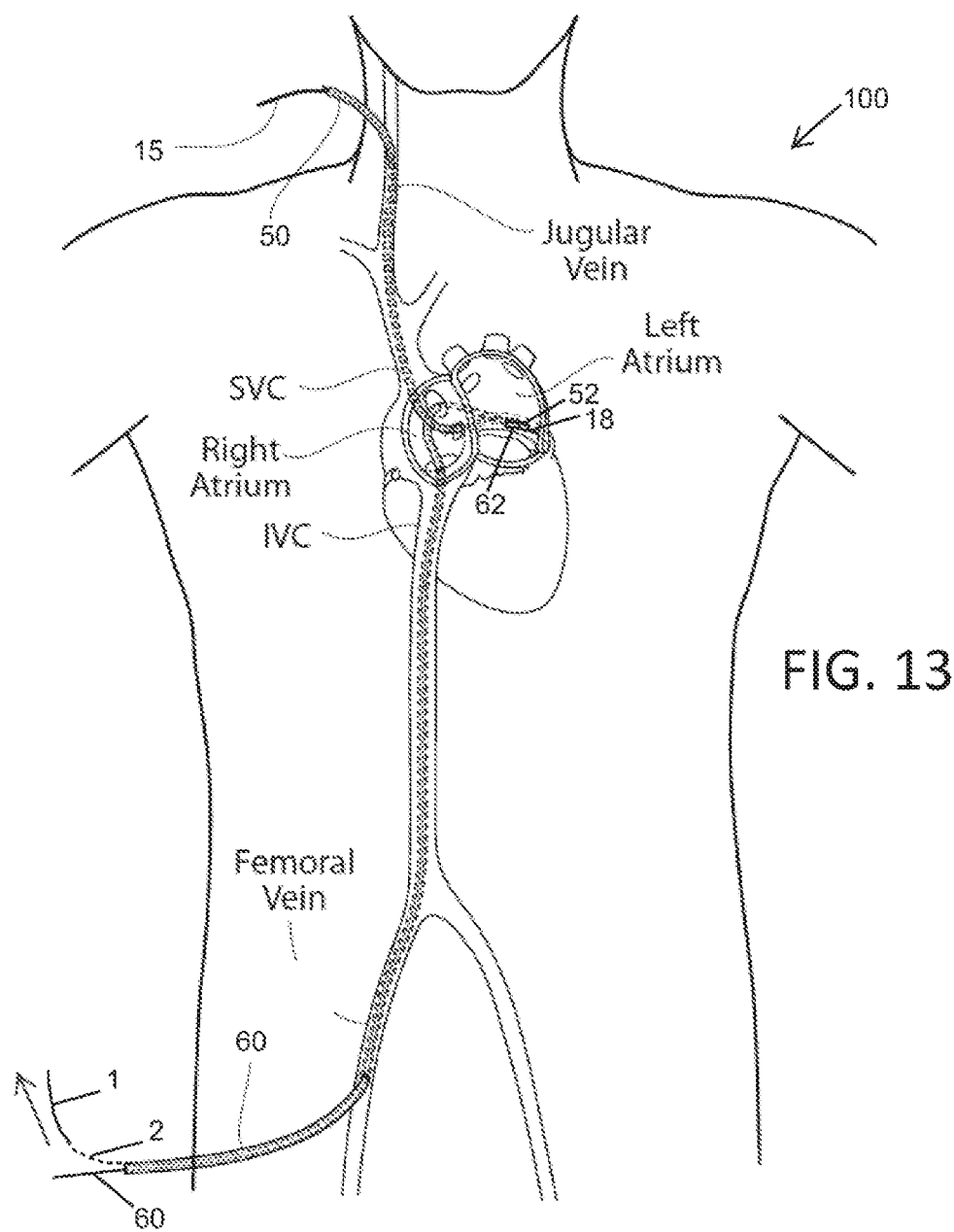
FIG. 13 shows another catheter-based delivery system for deployment of an implant system in which a bridging element attached to an anchor has been fed from a first vascular access point to a second vascular access point with first and second catheters in accordance with aspects of the invention.

Such a configuration allows the bridging element 12 to be advanced across the left atrium by advancing the puncturing needle wire 1 through the LA catheter 60 to exit from the femoral vein, while the magnetic heads remain magnetically coupled to each other, as shown in FIG. 13. As can be understood by referring to FIG. 13, the penetrating guidewire 1 has a length greater than the combined length of the catheters such that the guidewire 1 can be manually advanced externally from one vascular access point until the guidewire 1 exits the other vascular access point due to the stiffness of the guidewire 1. The guidewire 1 can be further retracted after exiting so as to pull the attached suture 2 through the vascular path until the suture 2 also exits the same vascular access point. This deployment approach can be understood further by referred to the following figures, which describe the implant and associated components in more detail as well as conventional approaches of delivery and deploying such implants.

Heart Implants for Treatment/Repair of a Heart Valve Annulus

A. Implant Structure

Figure 3A:
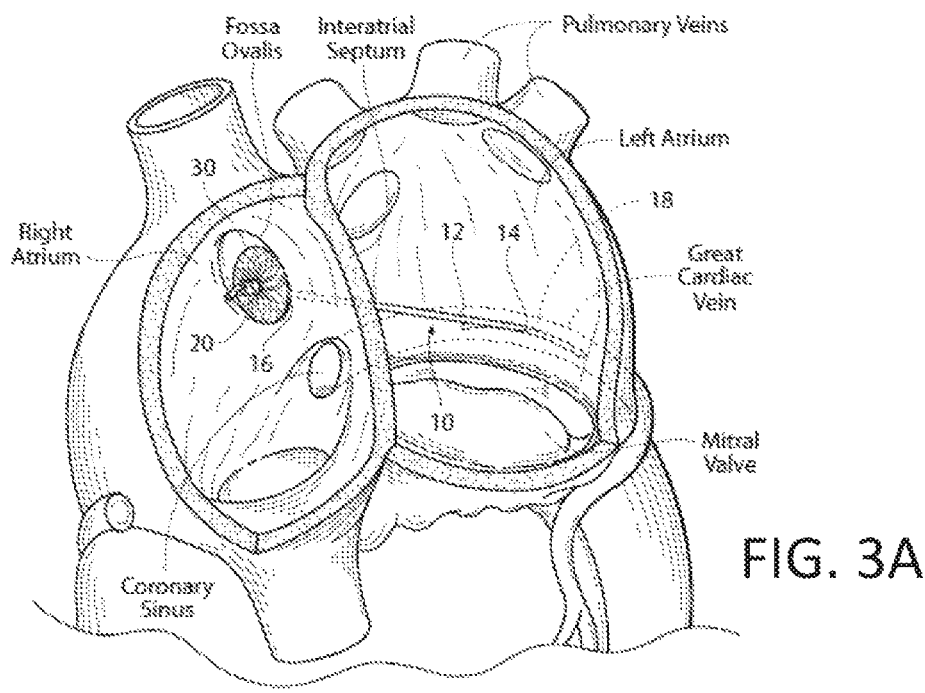
FIGS. 3A and 3B are anatomic anterior perspective views of the left and right atriums, with portions broken away and in section showing the presence of an implant system with an inter-atrial bridging element that spans the mitral valve annulus between a posterior anchor positioned in the great cardiac vein and an anterior anchor within the inter-atrial septum, which is suitable for delivery with the delivery catheter system described herein.
Figure 3B:
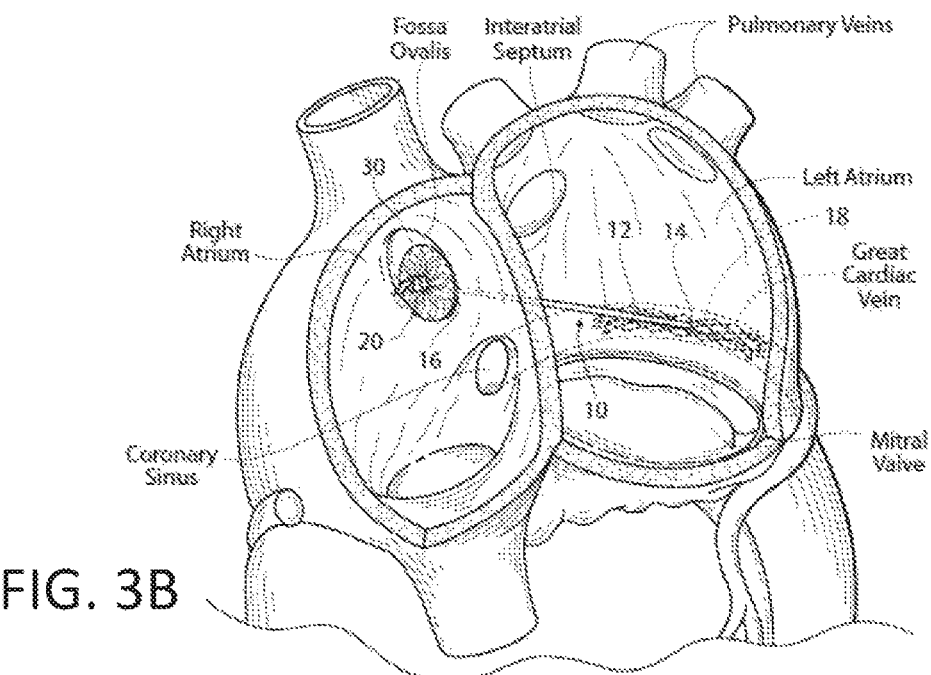

FIGS. 3A-3B show embodiments of an implant 10 that is sized and configured to extend across the left atrium in generally an anterior-to-posterior direction, spanning the mitral valve annulus. The implant 10 comprises a spanning region or bridging element 12 (formed by a portion of suture 2), the bridging element 12 having a posterior anchor region 14 and an anterior anchor region 16. The posterior anchor region 14 is sized and configured to allow the bridging element 12 to be placed in a region of atrial tissue above the posterior mitral valve annulus. The anterior anchor region 16 is sized and configured to allow the bridging element 12 to be placed, upon passing into the right atrium through the septum, adjacent tissue in or near the right atrium. For example, as is shown in FIGS. 3A-3B, the anterior anchor region 16 may be adjacent or abutting a region of fibrous tissue in the interatrial septum. As shown, the anchor site 16 is desirably superior to the anterior mitral annulus at about the same elevation or higher than the elevation of the posterior anchor region 14. In the illustrated embodiment, the anterior anchor region 16 is adjacent to or near the inferior rim of the fossa ovalis. Alternatively, the anterior anchor region 16 can be located at a more superior position in the septum, e.g., at or near the superior rim of the fossa ovalis. The anterior anchor region 16 can also be located in a more superior or inferior position in the septum, away from the fossa ovalis, provided that the anchor site does not harm the tissue in the region. Alternatively, the anterior anchor region 16, upon passing through the septum into the right atrium, may be positioned within or otherwise extend to one or more additional anchors situated in surrounding tissues or along surrounding areas, such as within the superior vena cava (SVC) or the inferior vena cava (IVC).

Figure 2A:
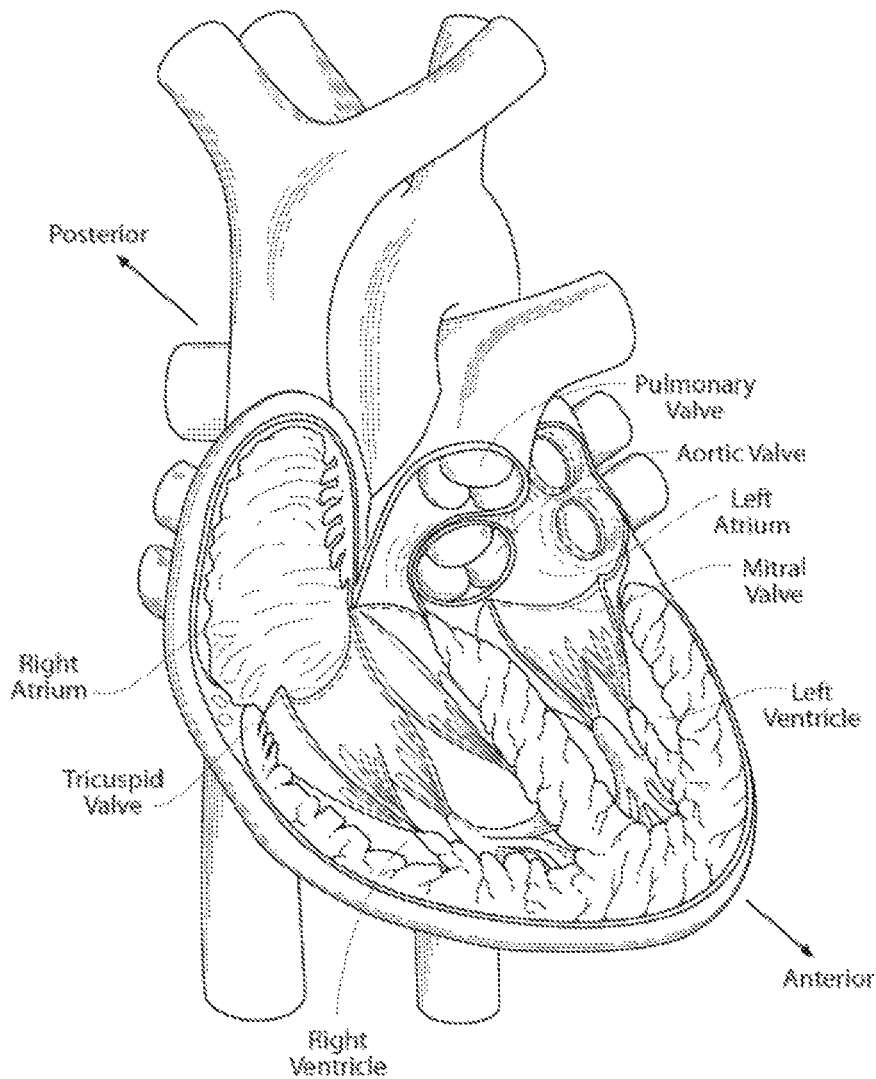
FIG. 2A is an anatomic anterior view of a human heart, with portions broken away and in section to view the interior heart chambers and adjacent structures.
Figure 2B:
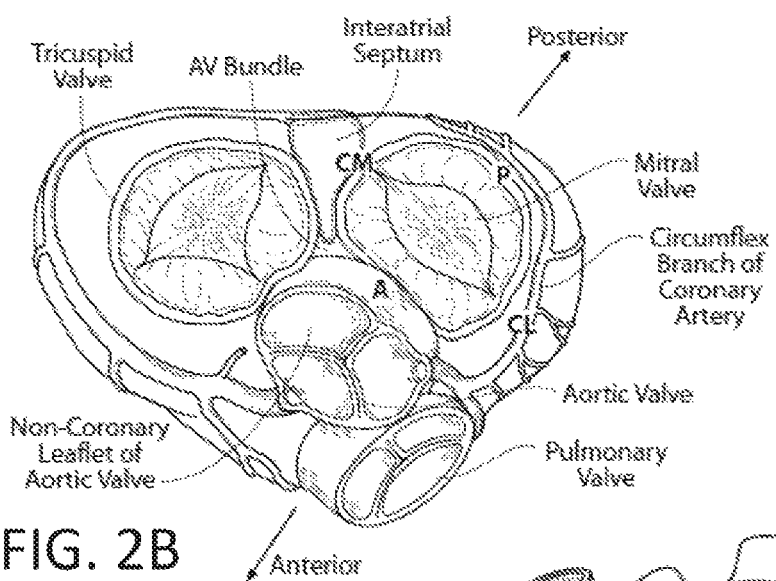
FIG. 2B is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
Figure 2C:
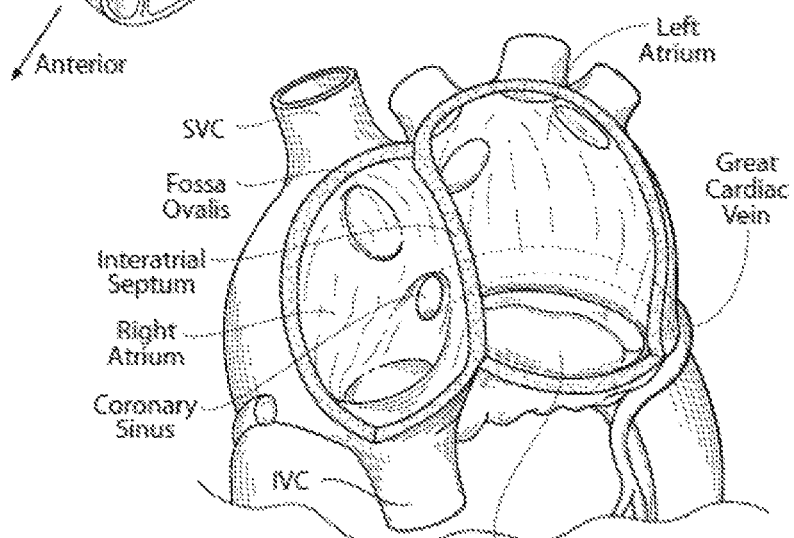
FIG. 2C is an anatomic superior view of a section of the human heart shown in FIG. 2B, with the tricuspid and mitral valves closed and the aortic and pulmonary valves opened during ventricular systole (ventricular emptying) of the cardiac cycle.
Figure 2D:
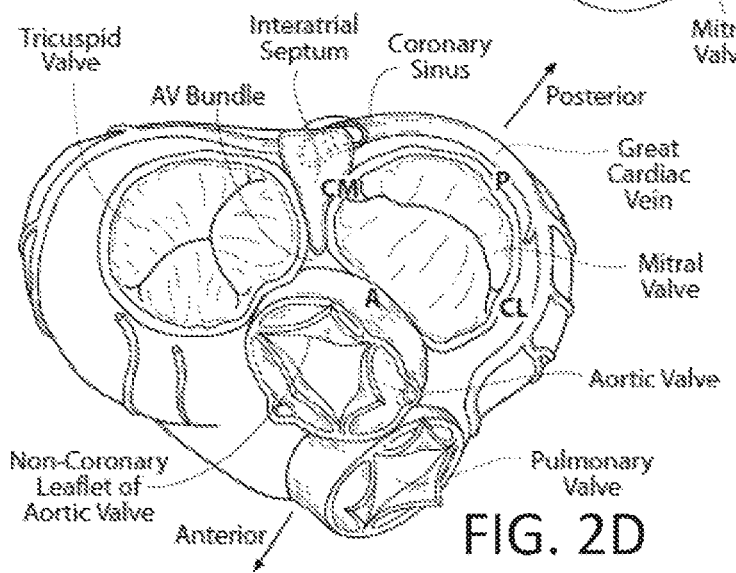
FIG. 2D is an anatomic anterior perspective view of the left and right atriums, with portions broken away and in section to show the interior of the heart chambers and associated structures, such as the fossa ovalis, coronary sinus, and the great cardiac vein.
Figure 2E:
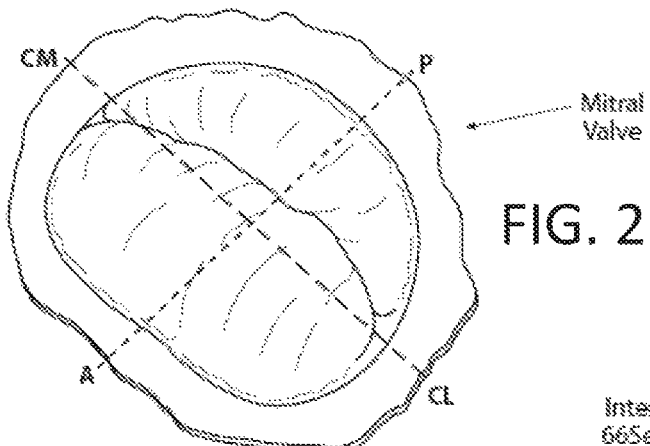
FIG. 2E is a superior view of a healthy mitral valve, with the leaflets closed and coapting at peak contraction pressures during ventricular systole.
Figure 2F:
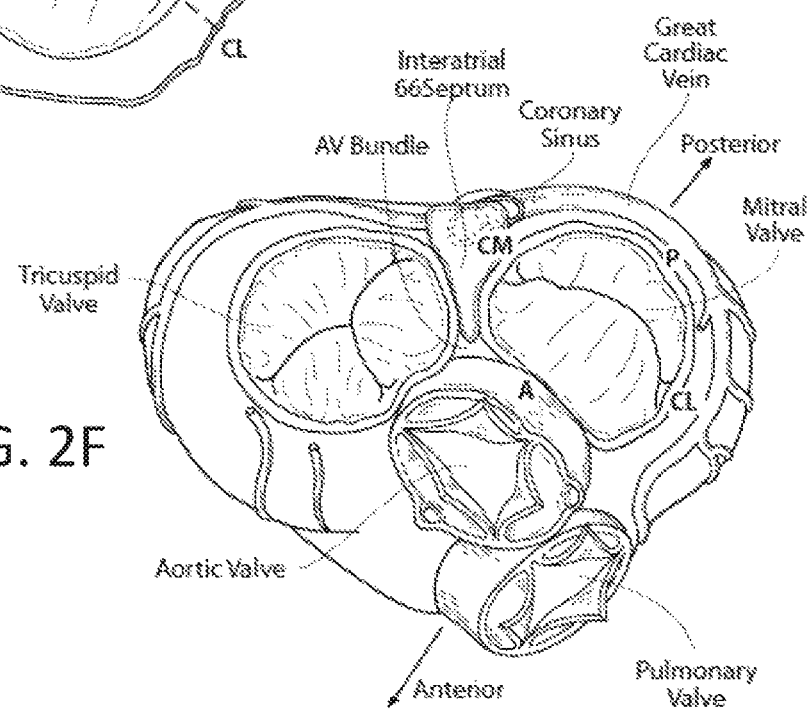
FIG. 2F is an anatomic superior view of a section of the human heart, with the normal mitral valve shown in FIG. 2E closed during ventricular systole (ventricular emptying) of the cardiac cycle.
Figure 2G:
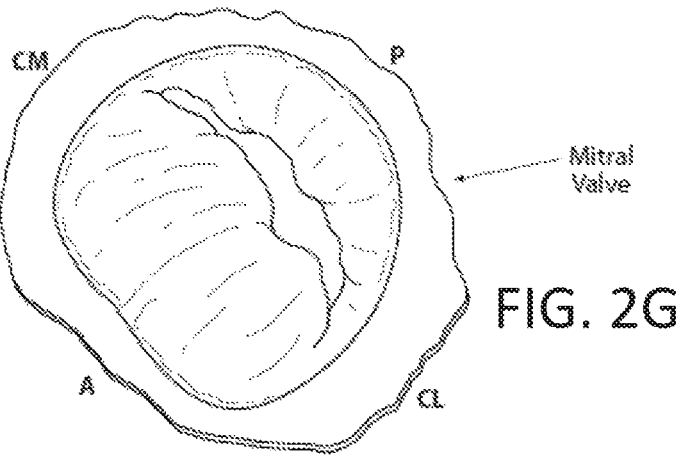
FIG. 2G is a superior view of a dysfunctional mitral valve, with the leaflets failing to coapt during peak contraction pressures during ventricular systole, leading to mitral regurgitation.

In use, the spanning region or bridging element 12 can be placed into tension between the two anchor regions 14 and 16. The implant 10 thereby serves to apply a direct mechanical force generally in a posterior to anterior direction across the left atrium. The direct mechanical force can serve to shorten the minor axis (along line P-A in FIG. 2E) of the annulus. In doing so, the implant 10 can also reactively reshape the annulus along its major axis (line CM-CL in FIG. 2E) and/or reactively reshape other surrounding anatomic structures. The mechanical force applied by the implant 10 across the left atrium can restore to the heart valve annulus and leaflets a more normal anatomic shape and tension. The more normal anatomic shape and tension are conducive to coaptation of the leaflets during late ventricular diastole and early ventricular systole, which, in turn, reduces mitral regurgitation.

In its most basic form, the implant 10 is made from a biocompatible metallic or polymer material, or a metallic or polymer material that is suitably coated, impregnated, or otherwise treated with a material to impart biocompatibility, or a combination of materials.

In some embodiments, the suture-wire includes a penetrating wire section having sufficient stiffness and compressive strength to penetrate tissue, which can be formed of a metal, such as Nitinol or stainless steel, or any suitable material, and further includes a more flexible, less stiff section that defines the bridging element, typically a substantially inelastic material, such as a thread-like or suture, or any suitable material.

B. The Posterior Anchor Region

The posterior anchor region 14 is sized and configured to be located within or at the left atrium at a supra-annular position, i.e., positioned within or near the left atrium wall above the posterior mitral annulus. In the illustrated embodiment, the posterior anchor region 14 is shown to be located generally at the level of the great cardiac vein, which travels adjacent to and parallel to the majority of the posterior mitral valve annulus. This extension of the coronary sinus can provide a strong and reliable fluoroscopic landmark when a radio-opaque device is placed within it or contrast dye is injected into it. The great cardiac vein also provides a site where relatively thin, non-fibrous atrial tissue can be readily augmented and consolidated. To enhance hold or purchase of the posterior anchor region 14 in what is essentially non-fibrous heart tissue, and to improve distribution of the forces applied by the implant 10, the posterior anchor region 14 may include a posterior anchor 18 placed within the great cardiac vein and abutting venous tissue.

C. The Anterior Anchor Region

The anterior anchor region is sized and configured to allow the bridging element 12 to remain firmly in position adjacent or near the fibrous tissue and the surrounding tissues in the right atrium side of the atrial septum. The fibrous tissue in this region provides superior mechanical strength and integrity compared with muscle and can better resist a device pulling through. The septum is the most fibrous tissue structure in its own extent in the heart.

As shown in FIGS. 3A-3B, the anterior anchor region 16 passes through the septal wall at a supra-annular location above the plane of the anterior mitral valve annulus. The supra-annular distance on the anterior side can be generally at or above the supra-annular distance on the posterior side. The anterior anchor region 16 is shown at or near the inferior rim of the fossa ovalis, although other more inferior or more superior sites can be used within or outside the fossa ovalis, taking into account the need to prevent harm to the septal tissue and surrounding structures.

Figure 5A:
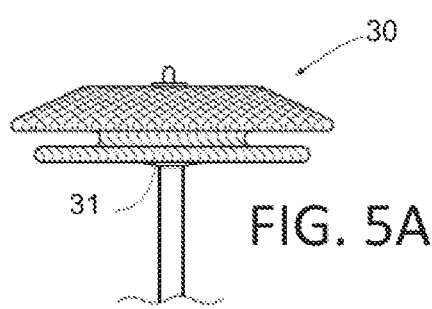
FIGS. 5A-5B show detail views of an example anterior anchor suitable for anchoring within the patent fossa ovalis of the inter-atrial septum within an implant.
Figure 10A:
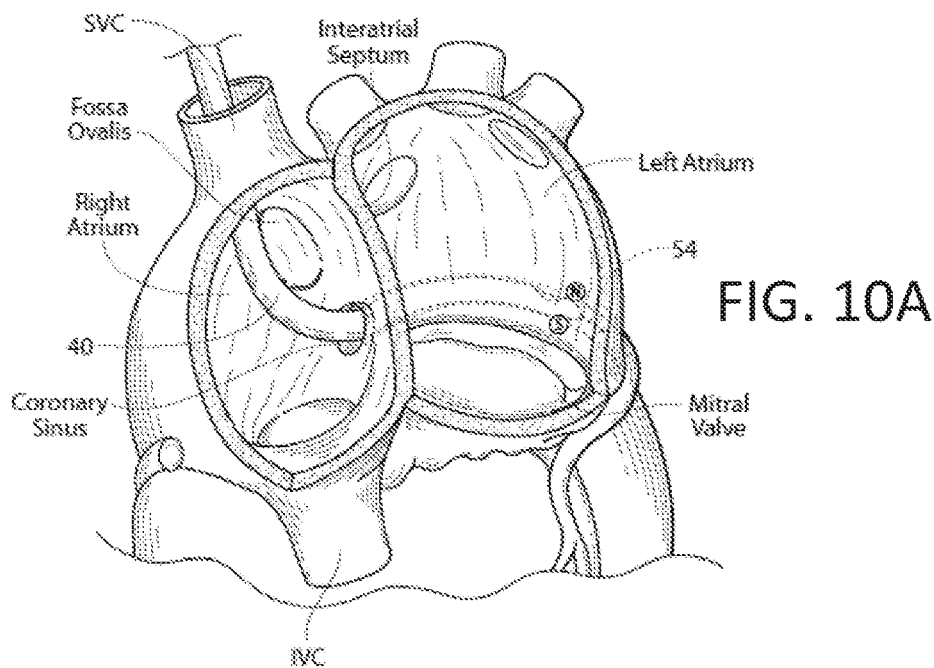
FIGS. 10A-12D show various components and steps of deploying an implant system, such as that shown in FIGS. 10A-10B, with a catheter-based delivery system in accordance with a conventional delivery approach.
Figure 10B:
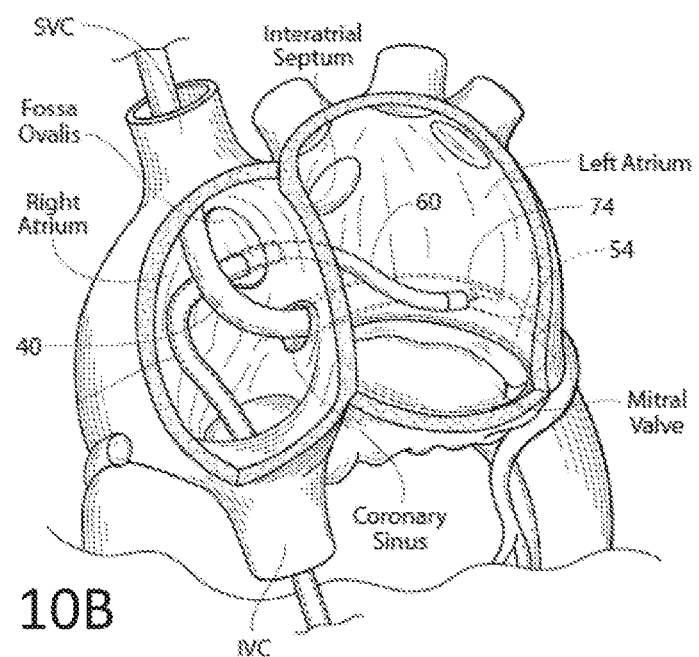

FIGS. 10A and 10B show the anterior anchor region including a septal member 30. The septal member 30 may be an expandable device and also may be a commercially available device such as a septal occluder, e.g., Amplatzer® PFO Occluder (see FIGS. 5A-5B). The septal member 30 preferably mechanically amplifies the hold or purchase of the anterior anchor region 16 in the fibrous tissue site.

D. Orientation of the Bridging Element

In the embodiments shown in FIGS. 3A-3B, the implant 10 is shown to span the left atrium beginning at a posterior point of focus superior to the approximate mid-point of the mitral valve annulus, and proceeding in an anterior direction in a generally straight path directly to the region of anterior focus in the septum. The spanning region or bridging element 12 of the implant 10 may be preformed or otherwise configured to extend in this essentially straight path above the plane of the valve, without significant deviation in elevation toward or away from the plane of the annulus, other than as dictated by any difference in elevation between the posterior and anterior regions of placement. It is appreciated that such implants can include bridging member with lateral or medial deviations and/or superior or inferior deviations and can include bridging members that are rigid or semi-rigid and/or substantially fixed in length.

E. Posterior and Anterior Anchors

Figure 4A:
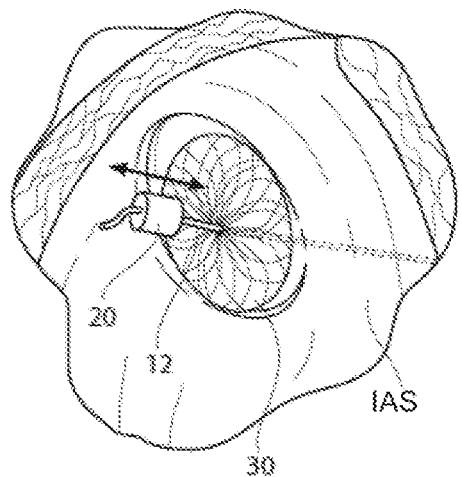
FIGS. 4A-4B are detail views showing an anterior anchor deployed within the fossa ovalis of the inter-atrial septum and the posterior anchor deployed in the great cardiac vein.
Figure 4B:
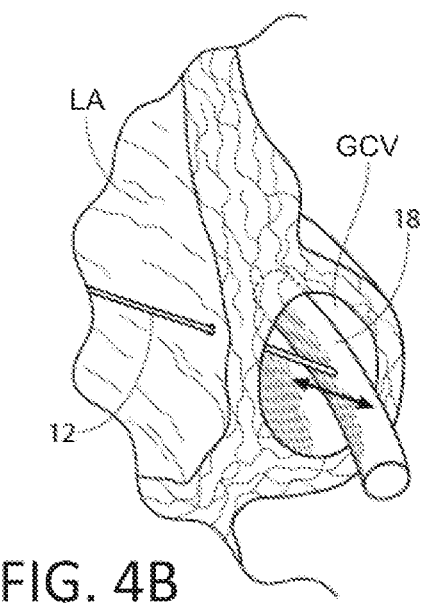

It is to be appreciated that an anchor as described herein, including a posterior or anterior anchor, describes an apparatus that may releasably hold the bridging element 12 in a tensioned state. As can be seen in FIGS. 4A-4B, anchors 20 and 18 respectively are shown releasably secured to the bridging element 12, allowing the anchor structure to move back and forth independent of the inter-atrial septum and inner wall of the great cardiac vein during a portion of the cardiac cycle when the tension force may be reduced or becomes zero. Alternative embodiments are also described, all of which may provide this function. It is also to be appreciated that the general descriptions of posterior and anterior anchors are non-limiting to the anchor function, i.e., a posterior anchor may be used anterior, and an anterior anchor may be used posterior. Thus, the bridging-element managed by the suture-wire management device may be attached to any type of anchor as desired.

Figure 6A:
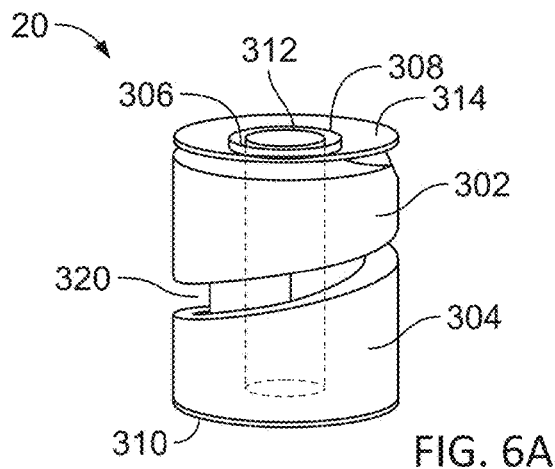
FIGS. 6A-6B show an example locking bridge stop for locking the bridging element relative the anterior anchor of the implant.
Figure 6B:
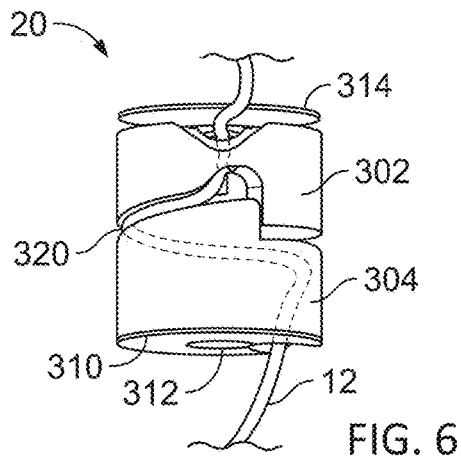

FIGS. 6A-6B show perspectives views of an example locking bridge stop 20. Each bridge stop 20 includes a fixed upper body 302 and a movable lower body 304 and positioned circumjacent a tubular shaped rivet 306. The upper body 302 and lower body 304 are held in position by the rivet head 308 and base plate 310 having a predetermined inner diameter 312, sized to allow bridge stop 300 to be installed over a guide wire. A spring, such as spring washer 314, is positioned circumjacent rivet 306 and between rivet head 308 and upper body 302, and applies an upward force on lower body 304, which is movable between a bridge unlocked position (see FIG. 6A), and a bridge locked position (see FIG. 6B).

Figure 7A:
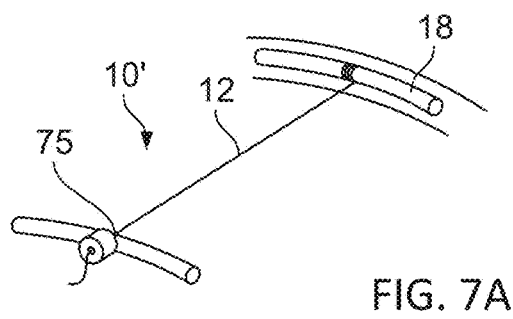
FIGS. 7A-7B show alternative examples of heart implants suitable for intravascular delivery in accordance with aspects of the invention.
Figure 7B:
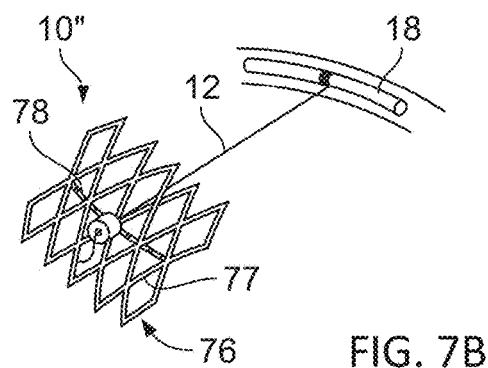

FIGS. 7A-7B show alternative heart implants suitable for delivery with the methods and delivery systems described herein. FIG. 7A shows an implant 10' having a T-shaped posterior anchor 18 in the great cardiac vein and T-shaped anterior anchor 70. The anterior T-shaped bridge stop 75 may be of a construction of any of the T-shaped bridge stop embodiments described. The T-shaped member 75 includes a lumen 75 extending through the T-shaped member 75 perpendicular to the length of the T-shaped member. The bridging element 12 may be secured by a free floating bridge stop as previously described. FIG. 7B shows an implant 10" having a T-shaped posterior anchor 18 in the great cardiac vein and a lattice style anterior anchor 76. The lattice 77 is positioned on the septal wall at or near the fossa ovalis. Optionally, lattice 77 may include reinforcement strut 78 to distribute tension forces over a greater area on the septal wall. It is appreciated that various other such implants could be devised that utilized the same concepts as in the above described implants for delivery and deployment with the systems and methods described herein.

Figure 8A:
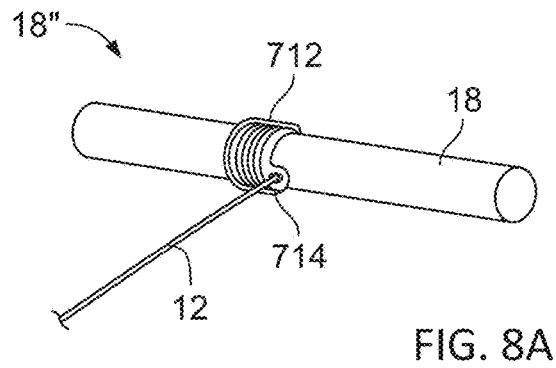
FIGS. 8A-8B alternative examples of posterior anchors attached to a bridging element suitable for intravascular delivery in accordance with aspects of the invention.
Figure 8B:
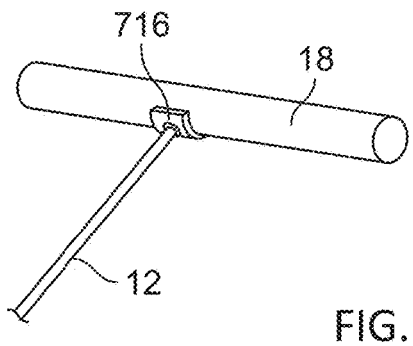

FIGS. 8A-8B show alternative methods of connecting the bridging element 12 to a T-shaped posterior anchor. FIG. 8A shows a T-shaped member 18 where the bridging element 12 is wound around a central portion of the T-shaped member. The bridging element 12 may be secured by adhesive 712, knot, or a securing band placed over the bridging element 12, for example. Alternatively, the bridging element 12 may first be threaded through a lumen 714 extending through the T-shaped posterior anchor 18 perpendicular the length of the T-shaped member. The bridging element 12 may then be wound around the T-shaped member, and secured by adhesive 712, securing band, or knot, for example. FIG. 8B shows a T-shaped member 18 where the bridging element 12 is welded or forged to a plate 716. The plate 716 may then be embedded within the T-shaped member 710. It is appreciated that various other couplings could be used to secure the bridging element 12 and posterior anchor 18 and facilitate delivery with the systems and methods described herein.

Figure 9A:
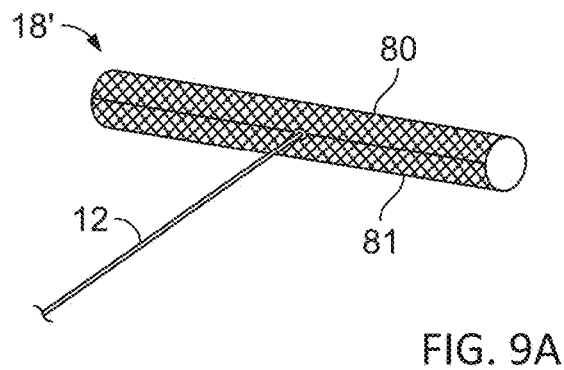
FIGS. 9A-9B show alternative examples of posterior anchors for heart implants suitable for intravascular delivery in accordance with aspects of the invention.
Figure 9B:
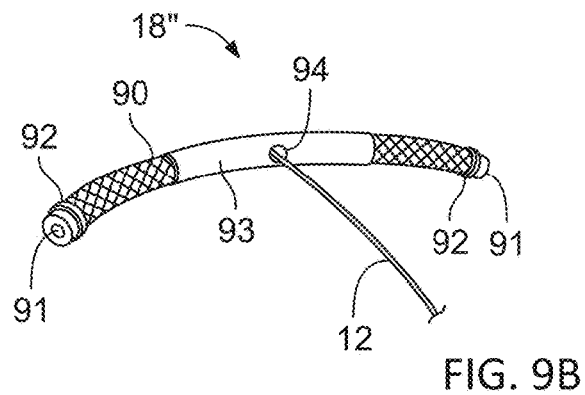

FIGS. 9A-9B depict alternative anchors suitable for use as posterior anchors within a heart implant. FIG. 9A is a perspective view of a T-shaped anchor 18' that includes an intravascular stent 80 and, optionally, a reinforcing strut 81. FIG. 9B depicts a T-shaped anchor 18" that includes a flexible tube 90 having a predetermined length, e.g., three to eight centimeters, and an inner diameter 91 sized to allow at least a guide wire to pass through. The tube 90 is preferably braided, but may be solid as well, and may also be coated with a polymer material. It is appreciated that various other type of anchors could be used.

II. General Methods of Delivery and Implantation

The implant systems 10 described herein lend themselves to implantation in a heart valve annulus in various ways. Preferably, the implant systems 10 are implanted using catheter-based technology via a peripheral venous access site, such as in the femoral or jugular vein (via the IVC or SVC) under image guidance, or trans-arterial retrograde approaches to the left atrium through the aorta from the femoral artery also under image guidance. As previously described, the implants 10 comprise independent components that are assembled within the body to form an implant, and delivered and assembled from an exterior the body through interaction of multiple catheters.

A. Conventional Delivery Approach

FIGS. 10A-12D show deployment of an implant 10 of the type shown in FIGS. 3A-3B by a percutaneous, catheter-based procedure, under image guidance using conventional methods into the femoral or jugular vein, or typically, a combination of both, such as any of those described in U.S. Patent Publication 2017/0055969.

Percutaneous vascular access is achieved by conventional methods into the femoral or jugular vein, or typically, a combination of both. As shown in FIG. 10A, under image guidance, a first catheter, or GCV catheter 40, is advanced into the great cardiac vein from a superior vena cava (SVC) route accessed from a neck vein (e.g. jugular vein) along a GCV guidewire 1. As shown in FIG. 10B, the LA catheter 60 is advanced from the right atrium via an inferior vena cava (IVC) accessed from a femoral vein, through the septum, typically at or near the fossa ovalis, and into the left atrium. The septal wall at the fossa ovalis is punctured with a trans-septal needle and a LA guide wire 74 is advanced through the septum into the left atrium. Typically a large bore (12-16 French) hemostasis sheath with a "Mullins" shape is placed in the LA to act as a conduit for placement for subsequent devices to placed or removed from the LA without injuring the tissues along the pathway to or in the LA. The LA catheter 60 is then advanced into the left atrium through this sheath.

Figure 11A:
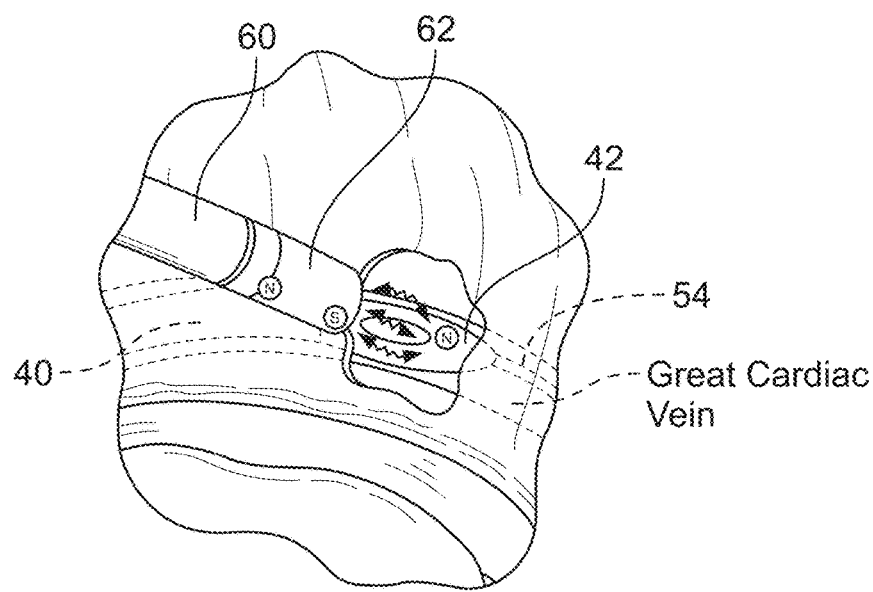
Figure 11B:
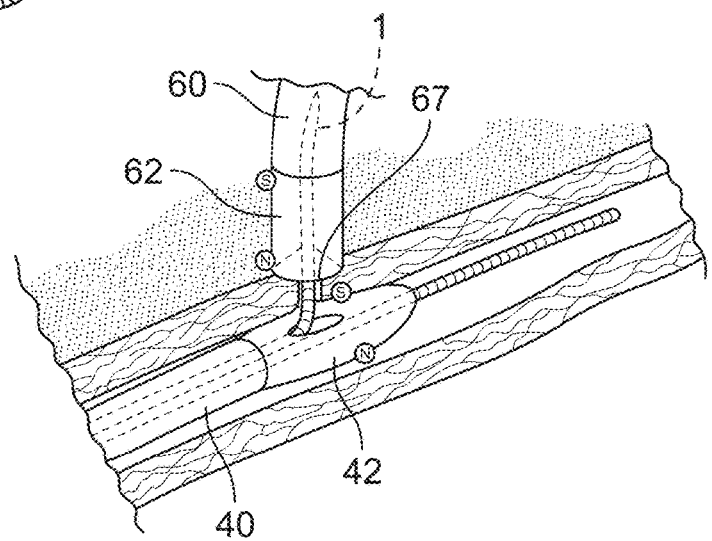
Figure 11C:
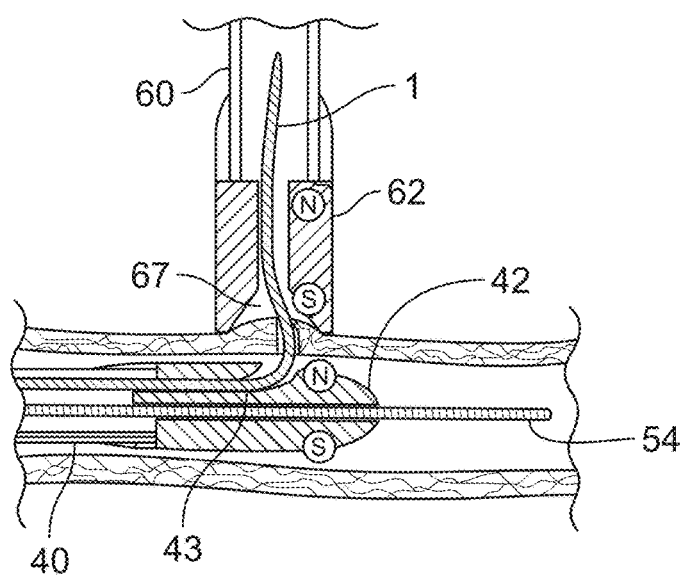

Each of catheters 40, 60 include a magnetic head 42, 62, respectively, disposed along a distal portion thereof, the magnetic heads being configured to facilitate magnetic coupling when positioned at a desired orientation and position across a tissue wall between the left atrium and the great cardiac vein. As shown in FIGS. 11A-11B, LA catheter 60 includes distal magnetic head having a N-S magnetic poles arranged axially along the catheter, while the GCV catheter 40 includes distal magnetic head having N-S magnetic poles arranged laterally relative a longitudinal axis of the catheter. This arrangement facilitate a transverse or perpendicular magnetic coupling between the respective catheters, as shown in FIGS. 11B-11C so as to allow passage of a penetrating element or guidewire, typically from a channel within one magnetic head into a corresponding channel of the other magnetic head. In this approach, the penetrating element is a puncturing guidewire 1 with a sharpened distal end. Typically, the puncturing guidewire 1 is advanced through a curved channel 43 within the magnetic head 42 of the GCV catheter 40 and enters a funnel-shaped channel 67 of magnetic head 62 of LA catheter 60. While in this embodiment, the magnetic head of GCV catheter 40 has a single magnet, it is appreciated that various other embodiments can include a magnetic head having additional magnets oriented to facilitate a desired alignment, for example, a three-magnet head in which a center magnet has magnetic poles oriented laterally to an axis of the catheter between two magnets with poles oriented axially, such as that shown in U.S. Patent Publication 2017/0055969.

Figure 12A:
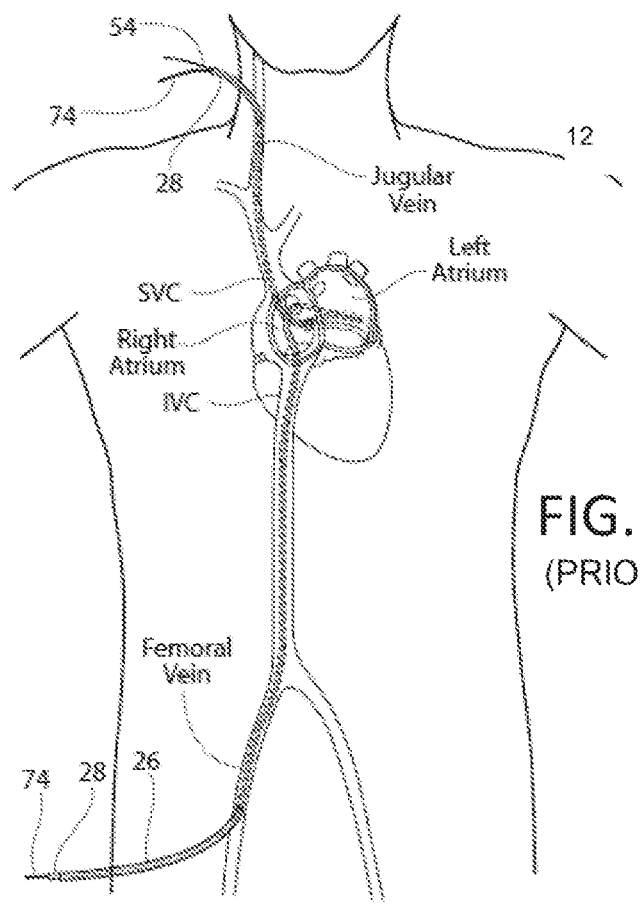
Figure 12B:
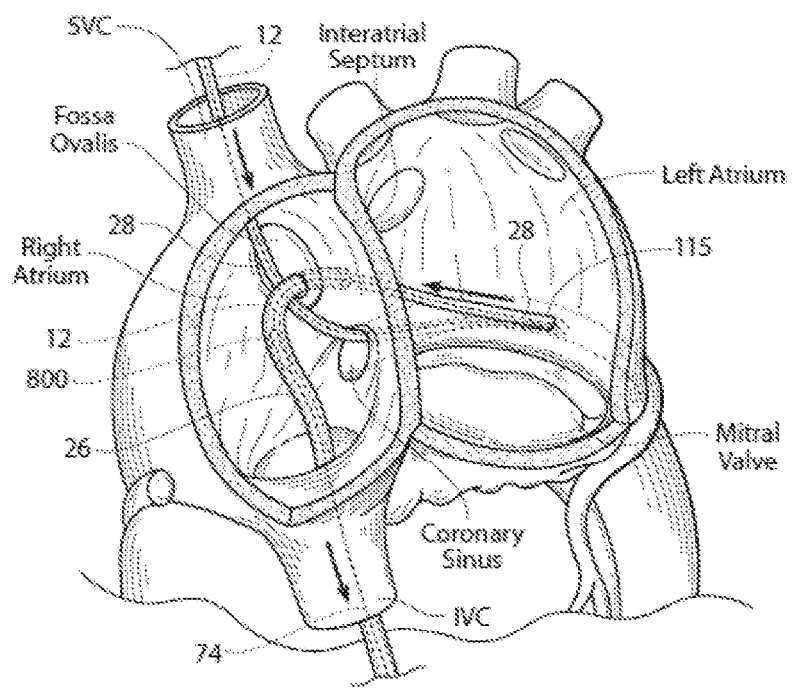
Figure 12C:
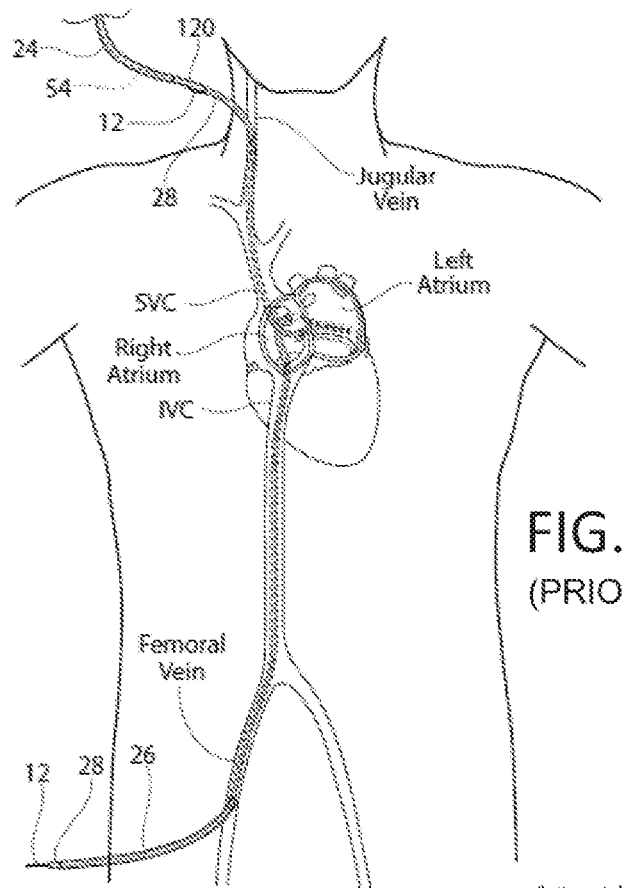
Figure 12D:
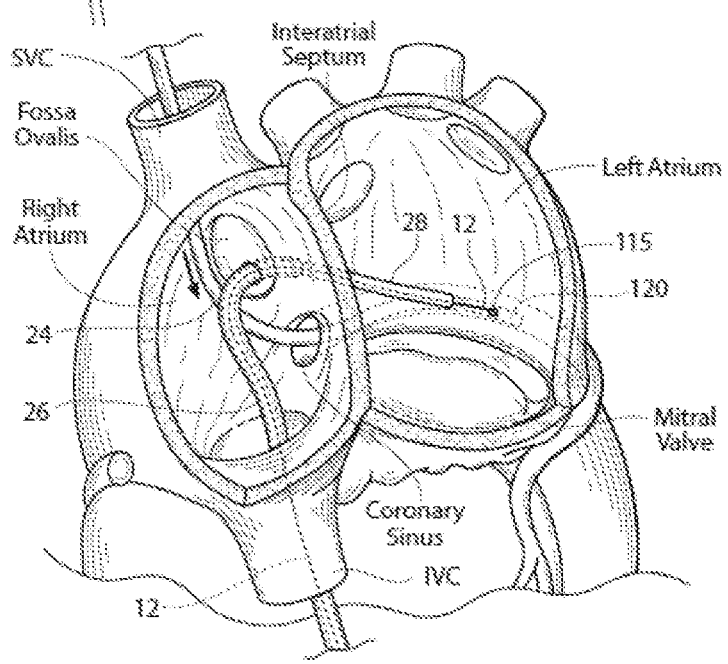

Next, as shown in FIG. 12A, the penetrating guidewire is advanced through the LA catheter 60 until it exits the femoral artery access point at the groin. The left atrium magnetic catheter A is then replaced by a very long exchange catheter 28, which is carefully pushed across the puncture site along the great cardiac vein to interface with the great cardiac vein magnetic catheter 40. The exchange catheter 28 is pushed simultaneously with removing the great cardiac vein magnetic catheter 40 to avoid exposing the puncturing wire to tissue. Exposure of the puncturing wire during this process could easily slice through tissue should the wire move or become tensioned during removal or replacement of one of the catheters. This process typically requires two operators, one operator pushes the exchange catheter while the other operator simultaneously removes the great cardiac vein magnetic catheter, often while utilizing visualization techniques to ensure the two catheters remain interfaced and the puncturing wire remains covered. Once the exchange catheter 28 is placed from neck to groin, the puncturing wire is removed and replaced with a left atrial extension guidewire 74, as shown in FIG. 12B.

Next, extension guide wire 74 is gently retracted, causing the bridging element 12 to follow through the vasculature structure. If the optional exchange catheter 28 is used (as shown in FIGS. 12A-12B), the extension guide wire 74 retracts through the lumen of the exchange catheter 28 without injuring tissues. The extension guide wire 74 is completely removed from the body at the femoral vein, leaving the bridging element 12 extending from exterior the body (preferably at the femoral sheath), through the vasculature structure, and again exiting at the superior vena cava sheath. The extension guide wire 74 may then be removed from the bridging element 12 by cutting or detaching the bridging element 12 at or near the interface coupling 800 between the bridging element 12 and extension guide wire 74. The anterior end of the extension guidewire 74 is attached to one end of the bridging element (e.g. suture material) while the other end of the bridging element is attached to the posterior anchor, which is retained within a posterior anchor delivery catheter 115. As can be seen in FIG. 12B, the extension guide wire 74 is gently retracted, causing the bridging element 12 to follow into the exchange catheter 28 and through the vasculature structure.

Posterior anchor 120 disposed within deployment catheter 24 is connected to the trailing end of bridging element 12 (which is the trailing portion of suture section 2 of suture-wire element) extending from the superior vena cava. While a T-shaped anchor is shown here, it is appreciated that various other types of posterior anchors can be used (e.g. stent, half-stent). The deployment catheter 24 is then positioned onto or over the GCV guide wire 54 and abutted against exchange catheter 28. The two-operator pushing and pulling process is repeated pushing the posterior anchor delivery catheter 115 while simultaneously removing the exchange catheter 28 so as to position the posterior anchor within the great cardiac vein and the bridging element extends across the left atrium. Optionally, the bridging element 12 may be pulled from the femoral vein region, either individually, or in combination with the deployment catheter 24, to facilitate advancement of the posterior anchor 120 and bridging element into position in the great cardiac vein and across the left atrium. The GCV guide wire 54 is then retracted letting the T-shaped anchor 120 separate from the GCV guide wire 54 and deployment catheter 24. Preferably under image guidance, and once separation is confirmed, the bridging element 12 is gently pulled to position the T-shaped anchor 120 in abutment against the venous tissue within the great cardiac vein and centered over the GCV access lumen 115. The deployment catheter 24 and exchange catheter 28 may then be removed. The T-shaped anchor 120 with attached bridging element 12 remain within the great cardiac vein. The length of bridging element 12 extends from the posterior T-shaped anchor 120, through the left atrium, through the fossa ovalis, through the vasculature, and preferably remains accessible exterior the body. The bridging element 12 is now ready for the next step of establishing the anterior anchor region 16, as previously described and as shown in FIGS. 16C-16D.

Once the posterior anchor region 14, bridging element 12, and anterior anchor region 16 configured as previously described, a tension is placed on the bridging element 12. The implant 10 and associated regions may be allowed to settle for a predetermined amount of time, e.g., five or more seconds. The mitral valve and mitral valve regurgitation are observed for desired therapeutic effects. The tension on the bridging element 12 may be adjusted until a desired result is achieved. The anchor 20 is then secured the bridging element 12 by use of a locking bridge stop 30 when the desired tension or measured length or degree of mitral regurgitation reduction is achieved.

B. Alternative Methods of Delivery and Associated Catheter Systems

In another aspect, an alternative anchor delivery catheter allows for improved delivery and deployment of the above-described implant with fewer catheters and improved ease of use as compared to the conventional approach described above. In some embodiments, the catheter systems includes an anchor delivery catheter having a distal magnet portion that facilitates access to a heart chamber from within an adjacent vasculature by passage of a penetrating guidewire to a magnetically couple catheters within the heart chamber. In some embodiments, the anchor delivery catheter is configured for delivery of the bridging element across the heart chamber (e.g. left atrium), once access is achieved, and subsequent deployment of the anchor within the vasculature (e.g. great cardiac vein). As described above, the bridging element is defined by the suture section, which is attached to the trailing end of the penetrating wire section while the other end of the suture section is attached to the posterior anchor disposed on a distal portion of the delivery catheter. This allows the bridging element to be advanced through the penetration between the heart chamber and vasculature by continued advancement of the suture-wire element from one vascular access point (e.g. jugular vein) to exit the body at the second vascular access point (e.g. femoral vein).

In some embodiments, for example as shown in FIG. 13, the above described anchor delivery is a GCV catheter 50 for delivery of the posterior anchor 18 within the GCV. Catheter 50 preferably includes a magnetic or ferromagnetic head 52 positioned along a distal portion of the catheter shaft. Optionally, a hub or handle with integrated suture-wire management can be positioned on the proximal end of the catheter. The catheter shaft may include a proximal section that is generally stiff to allow for torquability of the shaft, which can be of a solid or braided construction. The proximal section includes a predetermined length (e.g., fifty centimeters or more), to allow positioning of the shaft within the vasculature structure. A distal section, along which the distal portion is defined, may be generally flexible to allow for steerability within the vasculature or heart chamber. An inner diameter or lumen of the catheter shaft is preferably sized to allow passage of a GCV guide wire 15, and a penetrating guide wire as well as a bridging element. The GCV catheter 50 preferably includes a radio-opaque marker to facilitate adjusting the catheter under image guidance to align with the LA catheter 60. The magnetic or ferromagnetic head 52 is preferably polarized to magnetically attract or couple the distal end of the LA catheter 60, as described previously. Magnetic head 52 includes a guide channel formed therein to facilitate passage of the penetrating guidewire through the channel and into a corresponding channel in the magnetic head of the LA catheter 60.

Similar to the GCV catheter 50 the LA catheter 60 preferably includes a magnetic or ferromagnetic head 62 positioned on a distal end thereof. The catheter shaft may include a proximal and distal sections similar to those of catheter 50 described above. An inner diameter or lumen of the catheter shaft is preferably sized to allow passage of an LA guide wire 74, and additionally may accept the penetrating needle wire 1 passed from the GCV and subsequently the bridging element 12 attached thereto. The magnetic or ferromagnetic head 62 of the LA catheter 60 is polarized to magnetically attract or couple the distal end of the GCV catheter, for example, as shown in FIGS. 11A-11C.

Figure 17:
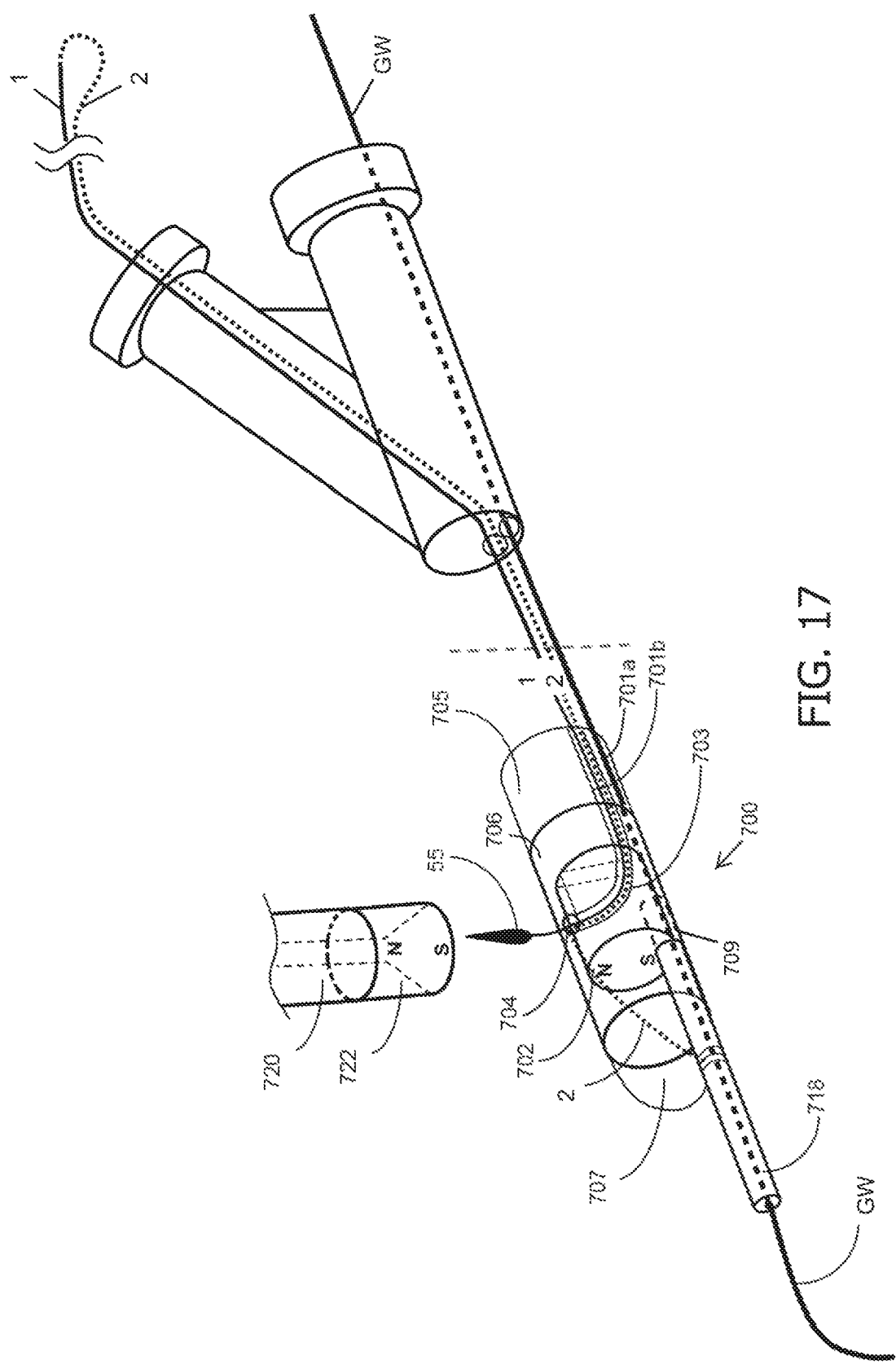
FIG. 17 illustrates an example catheter system for delivery and deployment of a heart implant in accordance with aspects of the invention.

While a particular configuration of magnetic heads are described above, it is appreciated that various other magnetic head configurations could be used, for example the configuration in FIG. 17 or any of these described in U.S. Patent Publication 2017/0055969.

1. Exemplary Implantation Methods

Access to the vascular system is commonly provided through the use of introducers known in the art. A 16F or less hemostasis introducer sheath (not shown), for example, may be first positioned in the superior vena cava (SVC), providing access for the GCV catheter 50. A second 14F or less introducer sheath (not shown and described above) may then be positioned in the right femoral vein, providing access for the LA catheter 60. Access at both the SVC and the right femoral vein, for example, also allows the implantation methods to utilize a loop guide wire. For instance, in a procedure to be described later, a loop guide wire is generated by advancing a LA guide wire through the vasculature until it exits the body and extends external the body at both the superior vena cava sheath and femoral sheath. The LA guide wire may follow an intravascular path that extends at least from the superior vena cava sheath through the interatrial septum into the left atrium and from the left atrium through atrial tissue and through a great cardiac vein to the femoral sheath.

Figure 14A:
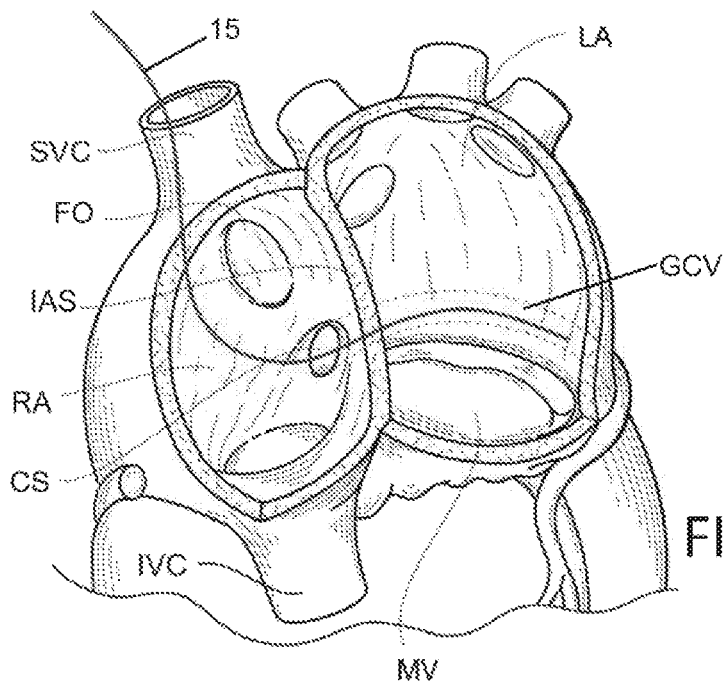
FIGS. 14A-16D illustrates sequential steps in delivery and deployment of a heart implant in accordance with aspects of the invention.

FIGS. 14A-16D illustrate a method of implantation utilizing a magnetic anchor delivery catheter in accordance with aspects of the invention. FIGS. 14A-14B depict positioning of the GCV anchor delivery catheter 50 within the great cardiac vein adjacent a posterior annulus of the mitral valve. As shown in FIG. 14A, under image guidance, the GCV guide wire 15 (e.g. a 0.035 inch guidewire), is advanced into the coronary sinus to the great cardiac vein along an SVC approach.

Figure 14B:
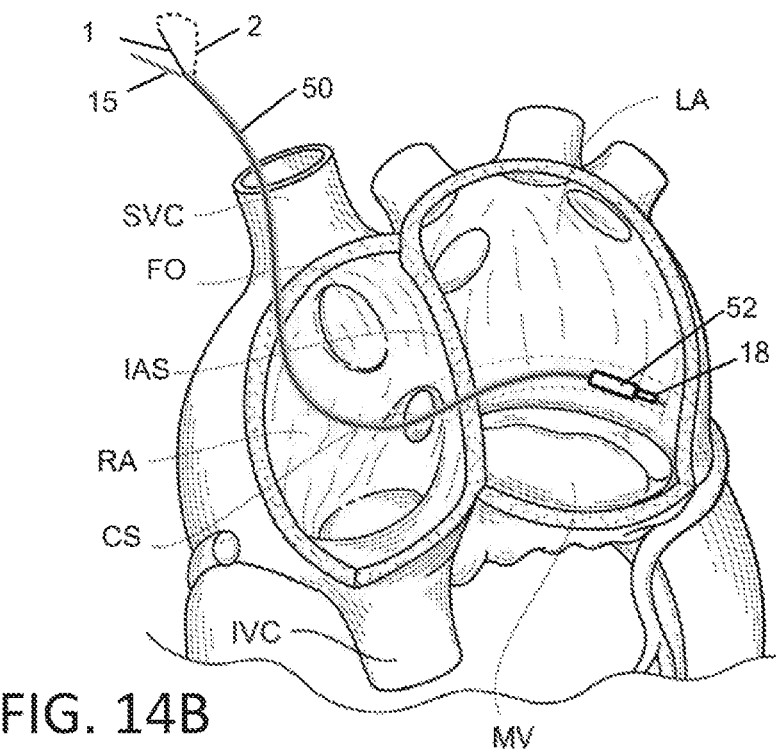

As shown in FIG. 14B, the GCV catheter 50 is advanced over the GCV guide wire 15 so that the distal magnetic head 52 and posterior anchor 18 are positioned at or near a desired location in the great cardiac vein, for example near the center of the posterior leaflet or posterior mitral valve annulus. The desired position for the GCV catheter 50 may also be viewed as approximately 2 to 6 centimeters from the anterior intraventricular vein takeoff.

Figure 14C:
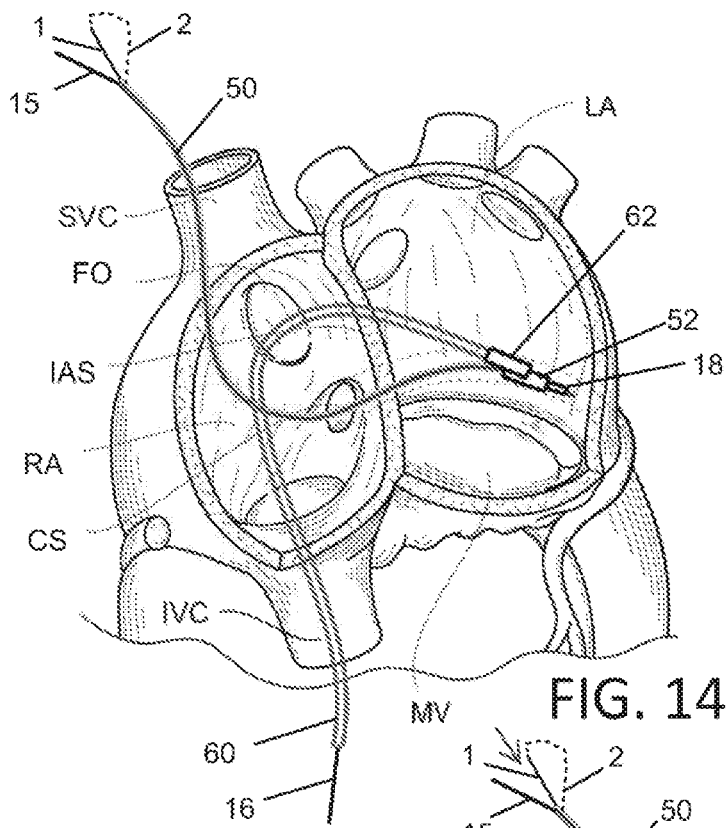

As shown in FIG. 14C, the LA catheter 60 is then deployed in the left atrium. From the femoral vein, under image guidance, the LA guide wire 16 (e.g., a 0.035 inch guidewire) is advanced into the right atrium. A 7F Mullins dilator with a trans-septal needle (not shown) can be deployed into the right atrium. The septal wall at the fossa ovalis can be punctured with a trans-septal needle and the guide wire 16 is advanced into the left atrium. The trans-septal needle is then removed and the dilator is advanced into the left atrium. The Mullins system is removed and then replaced with a 12F or other appropriately sized Mullins system. The 12F Mullins system is positioned within the right atrium and extends a short distance into the left atrium and the LA catheter 60 is advanced into the left atrium. After advancement of the LA catheter 60 into the left atrium, a distal magnetic head 62 of the catheter is positioned in the region adjacent the great cardiac vein so as to magnetically couple with the magnetic head 52 of GCV magnetic catheter 50, as shown in FIG. 11A. The magnetic heads automatically align the lumens of the LA catheter 60 and GCV catheter 50.

Figure 14D:
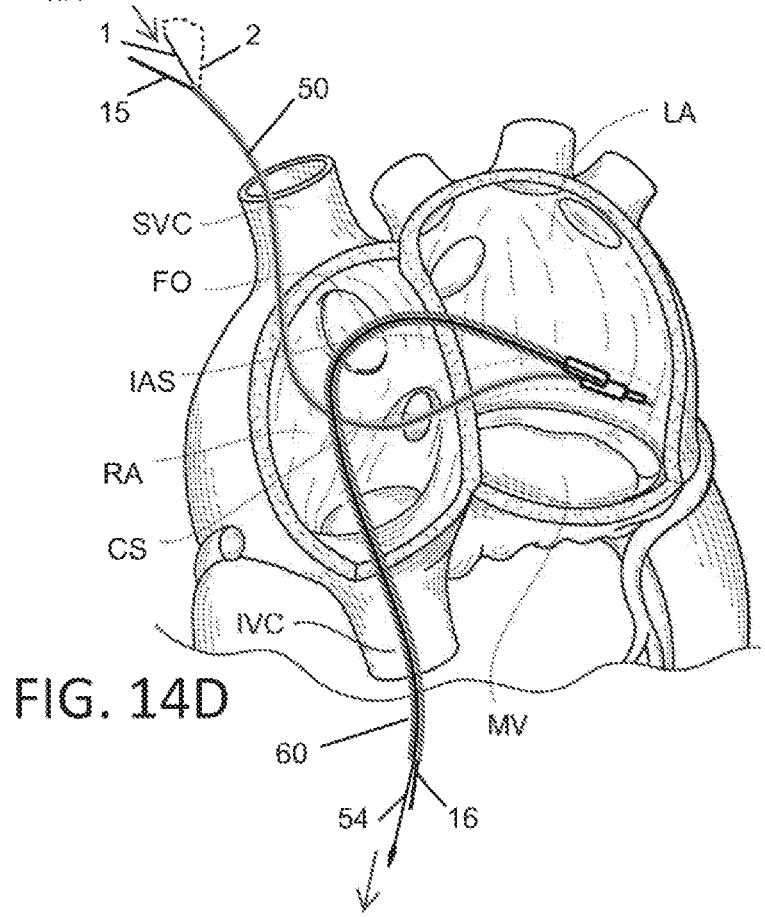

As shown in FIG. 14D, once magnetically coupled, puncturing wire 1 is advanced through GCV catheter 50 to penetrate the tissue wall between the great cardiac vein and the left atrium and enters a lumen of the magnetic head 62 of LA catheter 60. The operator continues to advance the puncturing guidewire 1 through a lumen of the LA catheter 60 until the guidewire exits the body (e.g. at the groin). Since the trailing end of the puncturing wire section 1 is attached to the one end of the suture section 2, the other end of the suture section being attached to posterior anchor 18, once the puncturing guidewire 1 exits the proximal end of the LA catheter 60, the puncturing wire 1 can be pulled proximally from the LA catheter 60 thereby pulling the suture section 2 through the GVC catheter 50, across the left atrium within the LA catheter 60 and through the vasculature to exit the body at the groin, all while the LA catheter 60 and the GVC catheter 50 remain magnetically coupled. This approach ensures the puncturing wire 1 and the suture section 2 remain covered while the being drawn through the vasculature over the delicate tissues of the heart, which avoids cutting or slicing the tissue with the bridging element and further avoids the laborious pushing and pulling procedure and use of an exchange catheter described in the conventional approach.

Figure 15A:
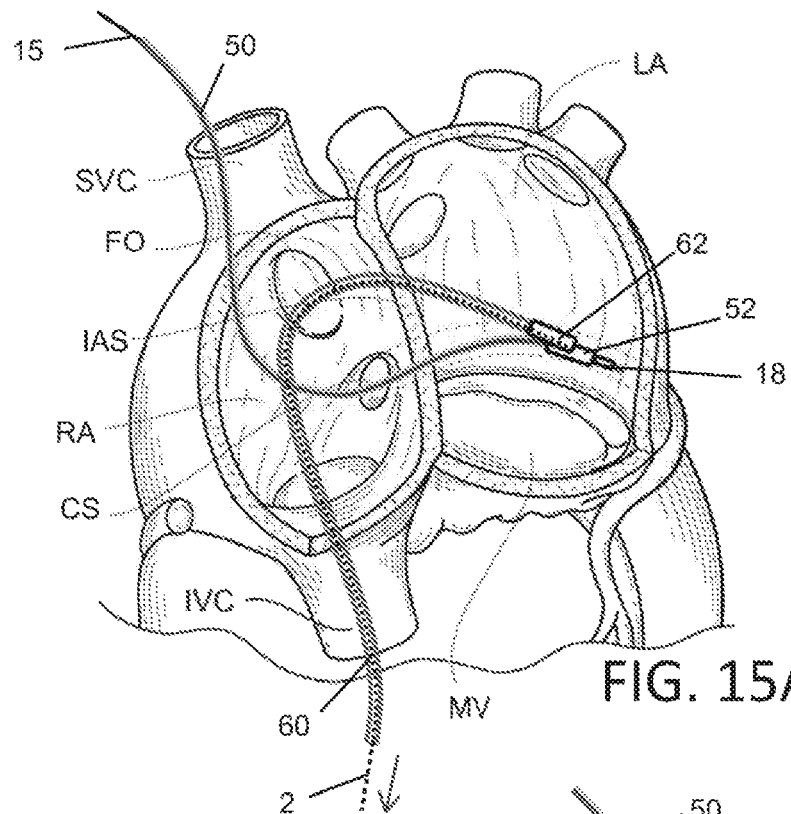
Figure 15B:
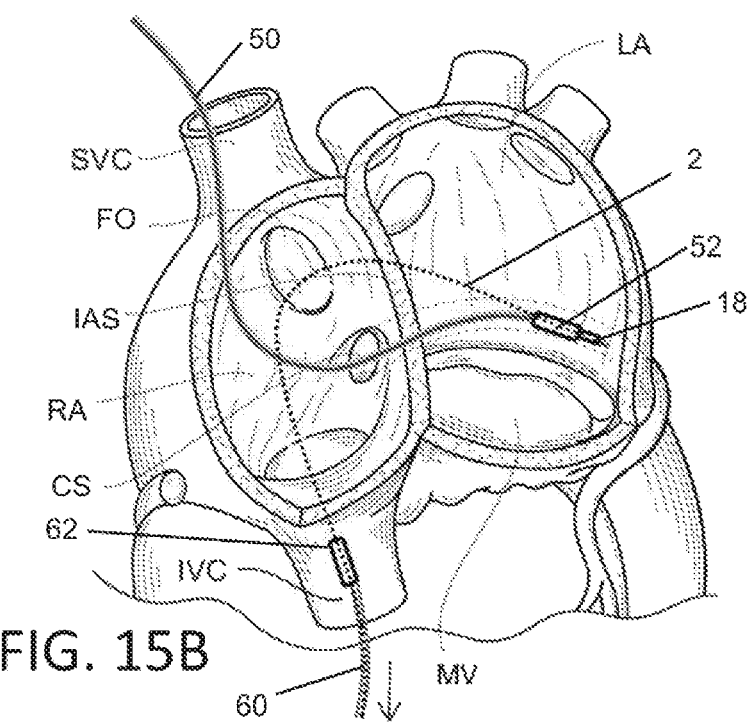

As shown in FIG. 15A, the suture section 2 extends from the posterior anchor 18 disposed within the distal portion of the GCV catheter 50, spans the left atrium and extends through the LA catheter 60 and exits the body at the femoral vein. The operator can gently tug the suture section 2 to remove any slack from the system and ensure it is properly positioned. In some embodiments, this action can also facilitate release of the posterior anchor 18 from the GCV delivery catheter 50. The LA catheter 60 can be decoupled from the GCV catheter 50 and withdrawn while the bridging element remains in place, as shown in FIG. 15B. Optionally, the LA catheter 60 can remain within the left atrium extending through the septum until the posterior anchor 18 is fully deployed.

Figure 15C:
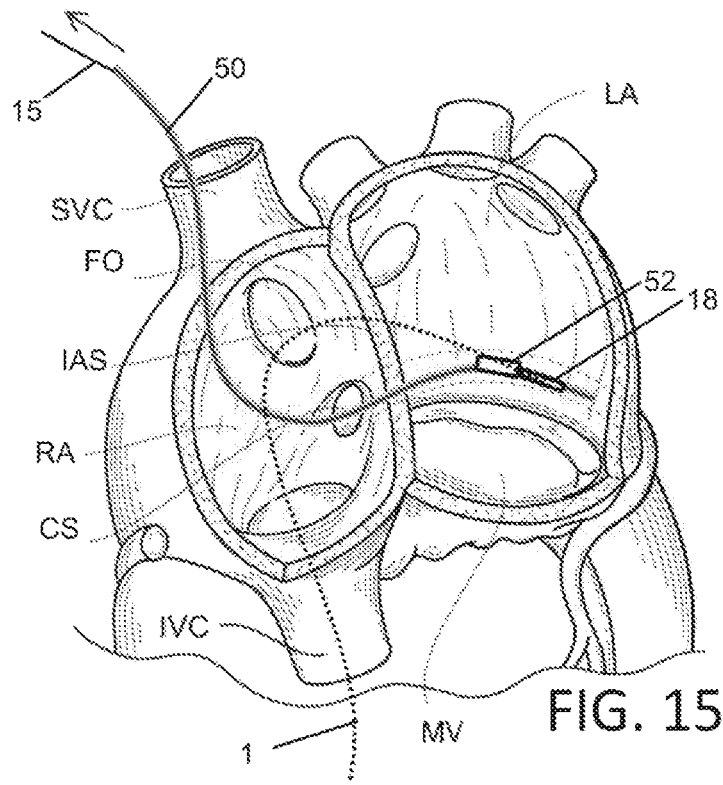
Figure 15D:
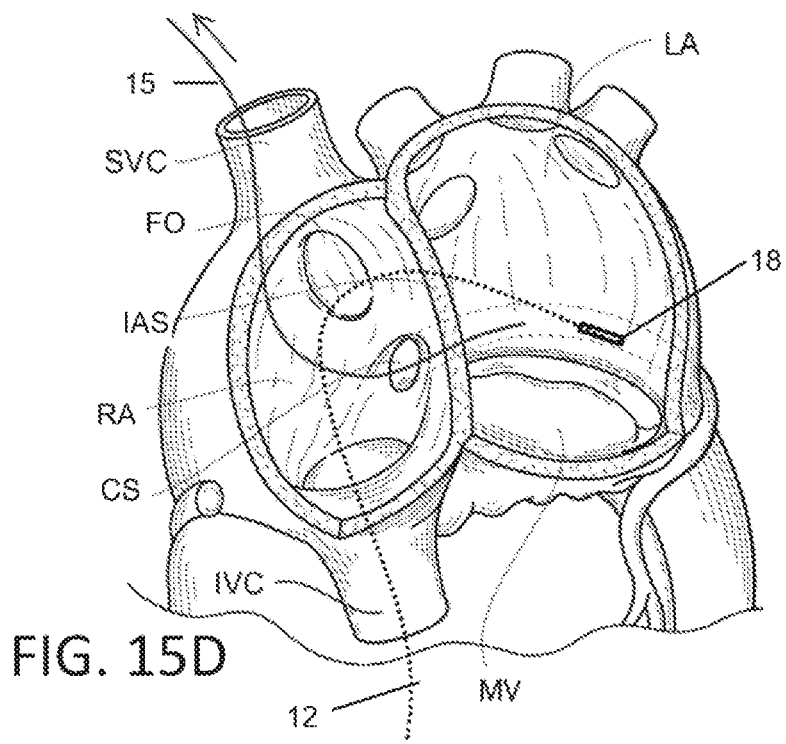

As shown in FIG. 15C, the GCV catheter 50 is adjusted, if needed, to position the posterior anchor 18 along the penetration for subsequent release from the catheter. The posterior anchor 18 can be released from the GCV delivery catheter 50 by proximally retracting the GCV guidewire 15 extending through the posterior anchor 18. Optionally, the catheter configuration can include a releasable coupling feature, such as a tether 903, that secures the posterior anchor 18 to the distal portion of GCV catheter 50 and extends from the proximal end so that an operator can proximally pull the tether to release the posterior anchor 18. Once the posterior anchor 18 is deployed, the GCV catheter 50 and GCV guidewire can be removed, as shown in FIG. 15D.

Figure 5B:
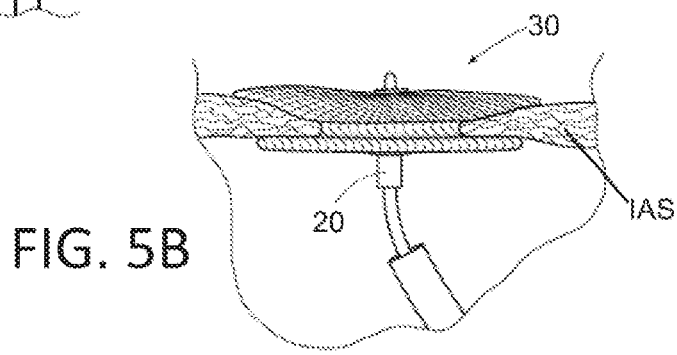
Figure 16A:
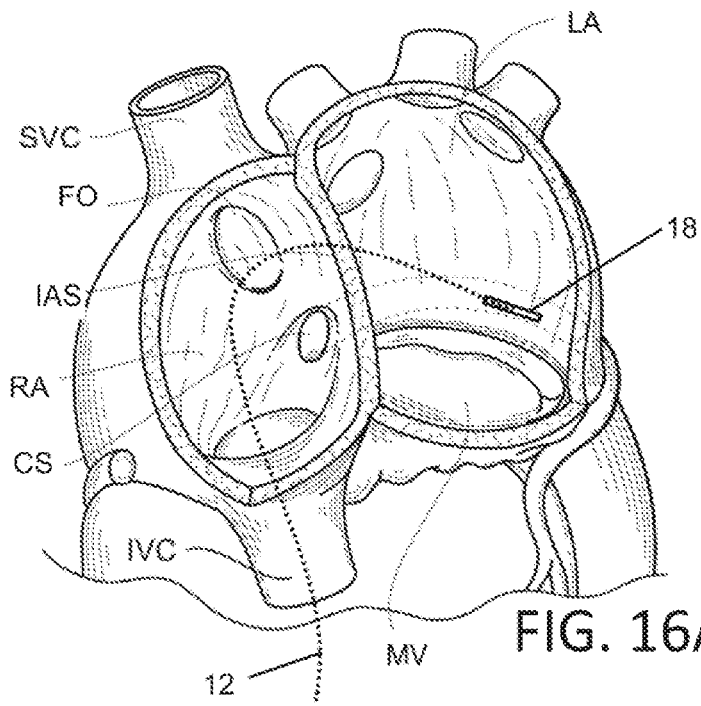
Figure 16B:
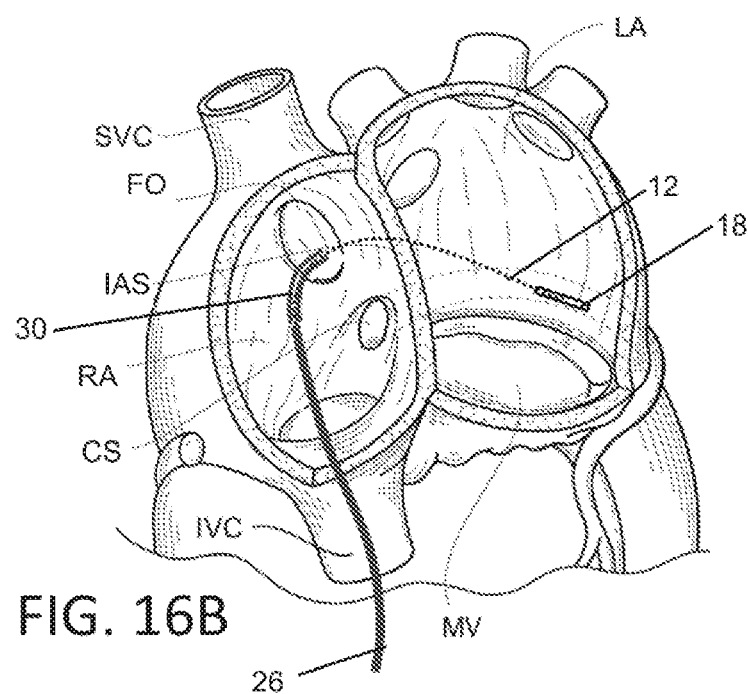
Figure 16C:
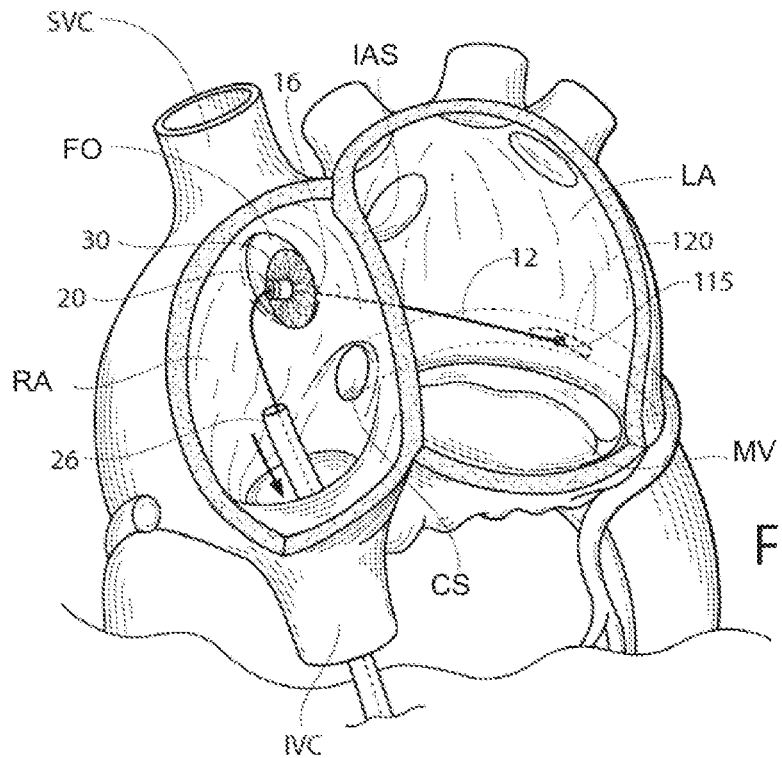
Figure 16D:
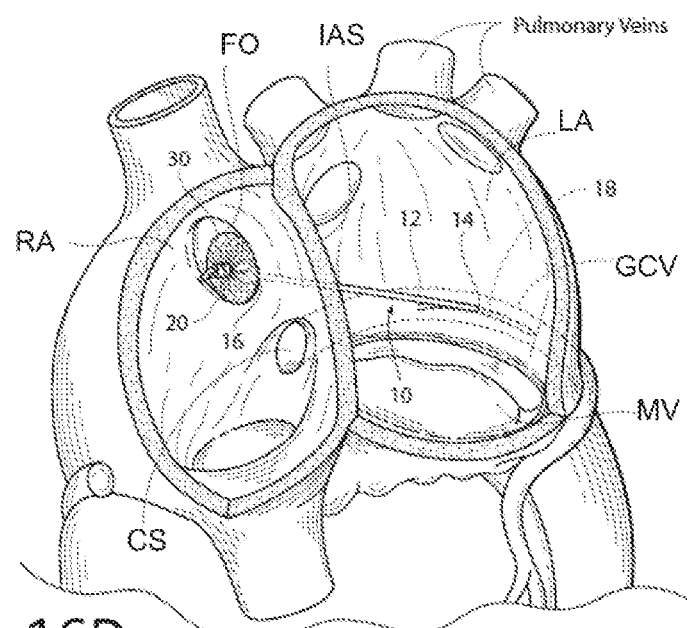

As shown in FIG. 16A, the posterior anchor 18 deployed within the great cardiac vein is attached to the suture section 2 spanning the left atrium and extending through the vasculature along the IVC route to exit from the femoral vein at the groin. Since the suture section 2 is not yet tensioned, there is little likelihood of cutting or damage to tissues at this point. Next, as shown in FIG. 16B, an anterior anchor delivery catheter 26 is advanced along the suture section 2 with the anterior anchor mounted with the bridging element passing through its central hub the delivery catheter 26 having an anterior anchor 30, collapsed inside the delivery sheath, disposed in a distal portion thereof, the bridging element passing through its central hub. The collapsed anterior anchor is guided to the FO or other suitable location along the septal wall and deployed, such as shown in FIG. 5B.

As shown in FIG. 16C, the anterior anchor 30 is deployed along the septal wall with a proximal locking bridge stop 20 through the delivery sheath. The length of the bridging element 12 can then be incrementally adjusted and held in place by the bridge lock 20 upon each adjustment until observation of the heart pumping indicates improved valve function. The excess bridging element 12 can then be cut with a cutting element of the catheter, or by use of a separate cutting catheter advanced along the bridging element 12. The LA delivery catheter 60 can then be removed, leaving the fully deployed implant 10 in place within the heart, as shown in FIG. 16D.

2. Exemplary Catheter Configurations

As discussed previously, one purpose of some such delivery catheter configurations is to facilitate deployment of the posterior anchor while keeping the bridging element totally within the protection of the magnetically connected catheters by combining the magnets and keeping the posterior anchor on one delivery catheter in the great cardiac vein. Examples of such delivery catheter configurations are detailed below. It is appreciated that any of the aspects or features described in certain embodiments may be utilized in various other embodiments in accordance with the concepts described herein.

FIG. 17 shows an exemplary anchor delivery catheter configuration in accordance with aspects of the invention. In particular, the catheter configuration allows for magnetically coupling with a corresponding catheter to establish access within a heart chamber from adjacent vasculature and delivering a heart implant in accordance with aspect of the invention. These example delivery catheters are configured for use within a GCV catheter 50, with the example delivery and deployment methods depicted above. It is appreciated that the following catheter configurations can include any of the various aspect described herein (e.g. length, materials, dimensions, etc.), but are not limited to the aspects described herein and could be configured as needed for a particular use or anatomy.

FIG. 17 shows a distal portion of a delivery catheter configuration 700 that includes a guidewire lumen 701a extending longitudinally to facilitate advancement of the catheter along a guidewire 1 positioned in the vasculature of the patient (e.g. within the great cardiac vein when the catheter configuration is utilized in a GVC anchor delivery catheter). The catheter can further include a puncture wire lumen 701b dimensioned to allow passage of the puncture wire section 1 and subsequent passage of suture section 2 attached thereto. The catheter includes a magnetic head 702 configured to magnetically couple with a magnetic head 722 of catheter 720 through a tissue wall therebetween. Magnetic head 702 is defined so that the magnetic poles of the magnetic heads are disposed laterally relative a longitudinal axis of the catheter so as to couple in a perpendicular orientation with magnetic head 722 of magnetic catheter 720, in a similar fashion as in FIG. 11C. The magnetic head 702 further includes a guide channel 703 defined to steer puncturing needle wire 1 upward through an exit hole 704 to direct the sharped distal tip 55 (e.g. flat tip) of the puncturing needle wire section 1 through the tissue wall and into magnetic head 722 of catheter 720. The dashed vertical line in FIG. 17 represents the point at which the delivery catheter extends outside the body. In any of these embodiments, the suture section 2 and puncturing needle wire 1 can extend through a Y-arm connector to facilitate independent manual control of the guidewire and the puncturing wire 1/suture section 2. In some embodiments the excess suture-wire (including the transition point between the needle wire section 1 and the suture section 2) can be wound within a suture-wire management device, which can be separate or incorporated into the catheter handle, as described further below. (The catheter shaft extending between the distal end portion and the Y-arm connector is not shown). In such embodiments, the length of the puncturing wire 1 is greater than the sum of both magnetic catheters, and the length of suture section 2 is at least long enough to extend from the posterior anchor to the second access site, so that when the puncturing wire is pulled from the second access site it pulls the suture section 2 out the second access site. In some embodiments, the suture section may be long enough that it remains outside the first access site until it is pulled out of the second access site, which is desirable in the unlikely event that the suture becomes disconnected from the needle wire section before the suture section is pulled out the second access site so that the operator may retrieve it by pulling on the proximal portion still out of the body. In this instance, the suture section would need to be as long as the sum of the length of the second catheter 60 and twice the length of the delivery catheter 50 since it needs to switch back as described above.

Catheter 700 includes a catheter shaft 705 along its length, which can be formed of any suitable material, to facilitate advancement of the catheter through the vasculature. As shown, the magnetic head 702 is formed with a notch or contoured recess in one side, which in this embodiment is opposite the exit hole 704, although could be located in any suitable location in embodiments. The notch, recess or groove 709 is configured to allow passage of the guidewire 1 and/or to receive at least a portion of posterior anchor 718. In this embodiment, posterior anchor 718 is defined as an elongate member having a longitudinal lumen through which the guidewire 1 extends. It is appreciated that a posterior anchor having a longitudinal lumen through which the guidewire 1 extends could be utilized in any of the embodiments described herein. It is further appreciated that the posterior anchor 718 could be positioned partly extending within a recess of the magnetic head, extending distally of the magnetic head (as shown) or proximally, or could extend proximally and proximally and distally of the magnetic head or could be disposed entirely proximal or entirely distal of the magnetic head. An outer jacket 706 covers the magnetic head 702 and includes an opening over exit hole 704 to allow passage of the penetrating wire section 1 therethrough. Typically, the outer jacket 706 is formed for a flexible polymer material and is defined to form a smooth interface with the catheter shaft 705. The outer jackets helps maintain the magnetic head 702 within the catheter and may extend at least partly over the posterior anchor 718 to help retain the posterior anchor 718 during advancement of the catheter through the vasculature. It is appreciated that the suture-wire management device can be used with different types of deployment system, including any of those described herein and any of those described in U.S. patent application Ser. No. 16/056,220 filed Aug. 6, 2018, the entire contents of which are incorporated herein for all purposes.

3. Bridge Cutting Catheters

Figure 18A:
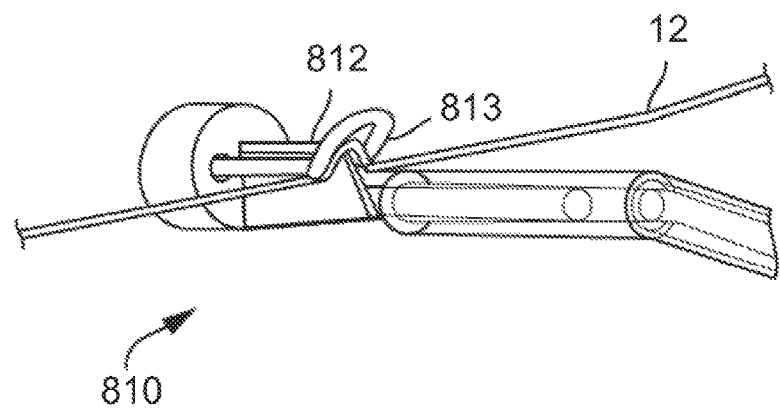
FIGS. 18A-19C depict example bridge cutting catheters, in accordance with aspects of the invention.

Delivery systems can further include a bridge element cutting device either incorporated into the catheter or as a separate catheter, examples of which are shown in FIGS. 18A-19C. FIG. 18A shows a bridge cutting catheter 810 to facilitate removal of a deployed implant. Bridge cutting catheter 810 includes a curve tipped stylet 811 within an inside diameter of the catheter shaft to facilitate steering of the cutting tip to suture bridge 12. The cutting tip includes a cutting blade 812 and a capture feature 813. The cutting blade 812 includes a sharpened cutting edge along one longitudinally extending side and an angled proximal facing end surface. The capture feature 813 is a loop that is angled so as to capture the bridging element 12 and direct the bridging element to the cutting edge when the cutting catheter is proximally retracted, thereby cutting the bridging element.

Figure 18B:
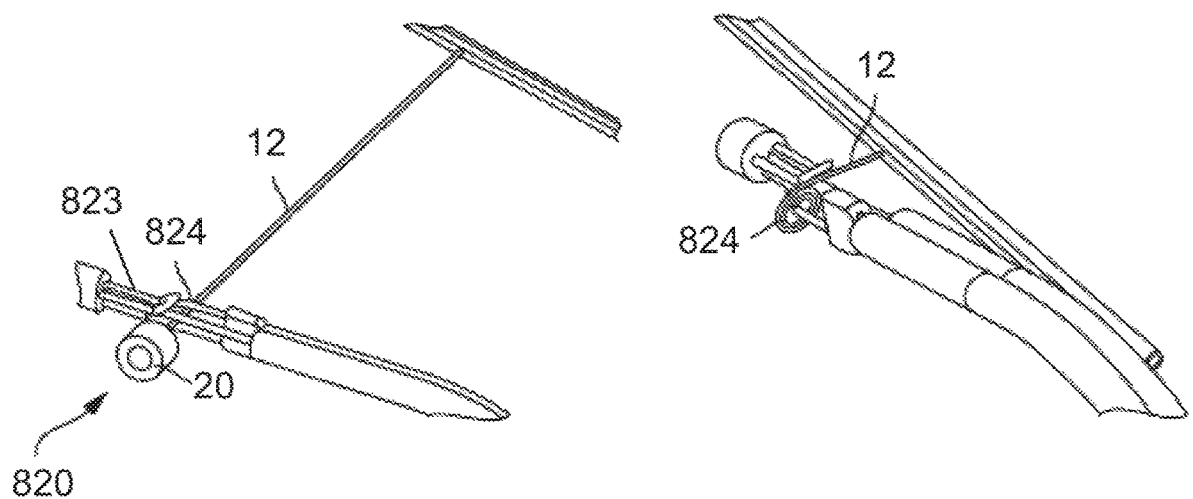
Figure 18C:
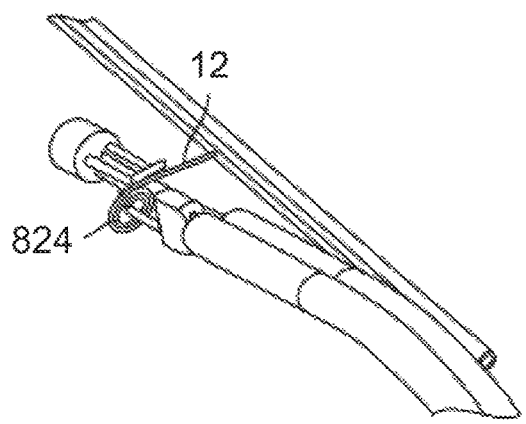

FIGS. 18B-18C shows a bridging cutting catheter 820 with suture grip 824 for cutting the bridging element and removing excess suture after cutting, in accordance with aspects of the invention. Similar to the bridge cutting catheter in FIG. 18A, the catheter includes a cutting head with a cutting blade and a capture loop 823 configured to operate in a similar manner as described above. This catheter further includes a suture grip 824 to facilitate removal of excess suture. The suture grip 824 can be configured to hold the bridging element (e.g. by friction fit, or between opposable members) and to wind up excess bridging element by rotation of an element extending through a shaft of the catheter. After initial cutting of the bridging element 12 with the cutting element, as shown in FIG. 18B, suture grip 824 is actuated by rotation of a rotatable member extending through the shaft, which winds up excess suture and also moves the cutting catheter adjacent the posterior anchor, as shown in FIG. 18C. As suture grip 824 holds excess suture taut, a second cut can be made with the cutting tip, thereby removing a majority of the bridging element 12. The excess suture is retained on the suture grip and removed upon removal of the cutting catheter.

Figure 19A:
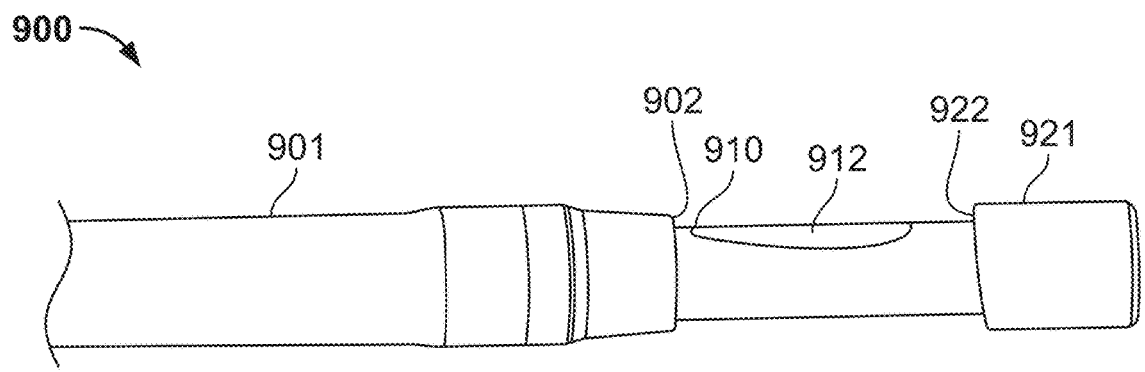
Figure 19B:
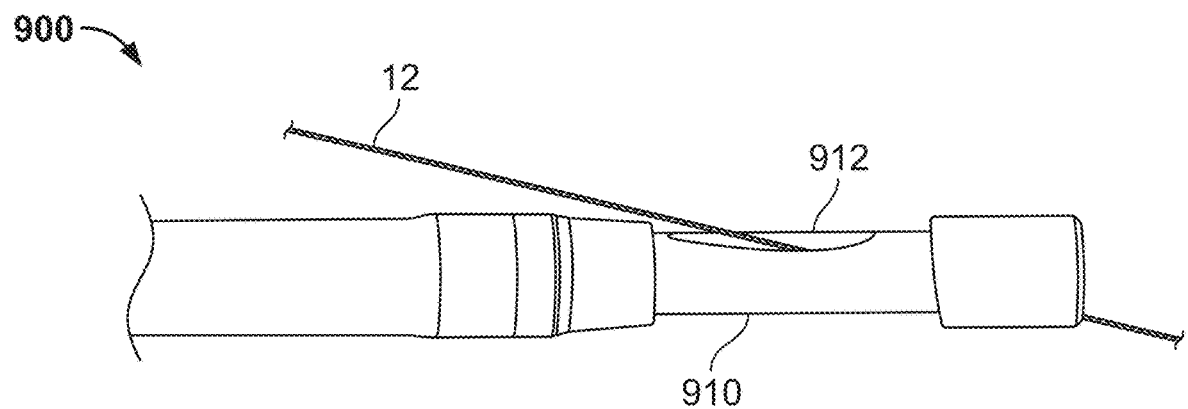
Figure 19C:
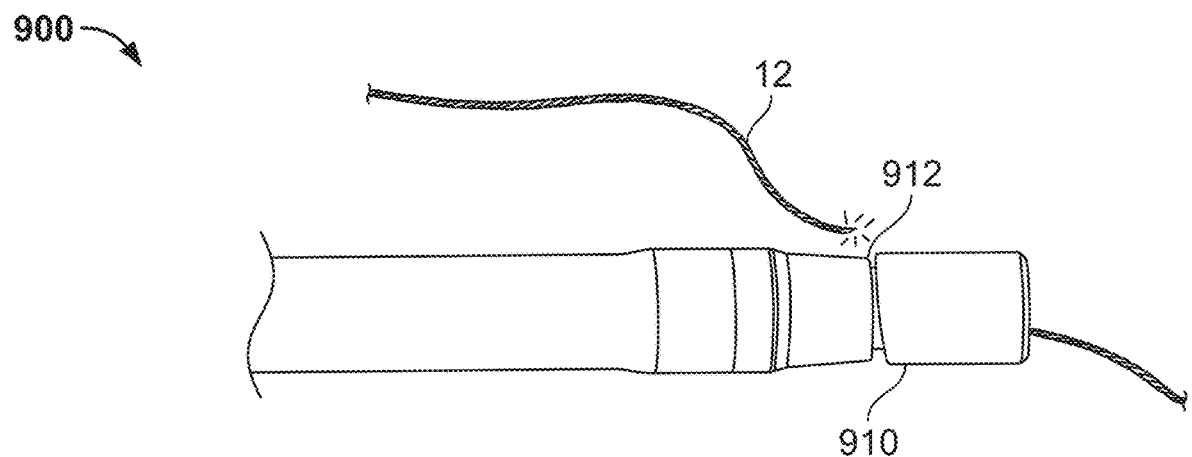

FIGS. 19A-19C shows an another type of cutting catheter, in accordance with aspects of the invention. As shown in FIG. 19A, cutting catheter 900 includes an outer catheter shaft 901 having a sharp beveled cutting tip 902 at a distal end thereof. The catheter shaft 901 is slidable along an inner shaft 910 toward a distal catheter tip 921 having a proximal facing blunt cutting surface 922 for engagement with the sharp cutting tip of the outer shaft 901. The inner shaft 910 includes a suture lumen opening 912 for passage of the suture 12 therethrough. The cutting action can be a combination of pressure and rotation of cutting tip 902 against blunt cutting surface 922 with the suture pinched in between. FIG. 19B shows the outer shaft 901 locked in an open position, which allows the catheter to be guided over the suture to a desired cutting location without premature cutting. FIG. 19C shows the suture 12 having been cut by the sharp beveled tip 902 engaged against the blunt cutting surface 922.

III. Suture-Wire Element Management Devices

As described above, the deployment system utilizes a suture-wire element having a relatively stiff needle section and a more flexible suture section. In the embodiments described above, a portion of the suture section defines the bridging element of the implant that spans across the atrium between posterior and anterior anchors. Given that each section of the suture-wire element is advanced from one vasculature access point to exit the body through another vascular access point, the combined length of the suture-wire bridge element is substantial and can be difficult to store and manage during the delivery and deployment process described above. Further complicating issues, care must be taken to avoid contamination of the suture-wire while handling since it is passed through the body. Conventional methods and devices for storing/dispensing suture or wire material cannot feasibly be used with a suture-wire bridge element having different sections with differing mechanical properties (e.g. stiffness, flexibility, compressive strength), such as the suture-wire element described herein. In one aspect, the invention pertains to a device pertains to management of a bridging element that includes sections of differing stiffness.

A. Suture-Wire Bridging Element

As described above, the suture-wire element for the implant delivery catheter system includes at least two sections having differing properties and is used as a bridging element within a heart implant. The first section is a stiffer needle like element or "wire section", preferably made from super-elastic NiTi wire, that has a distal puncturing tip. It is flexible enough to pass through the perpendicular connection at or near the tips of two magnetically connected catheters, as shown in the embodiment of FIGS. 14C-14D. In some previous embodiments, the puncturing function is performed by a separate device or feature at a distal end of the needle wire section or by an entirely separate device. In other embodiments, the needle wire section itself has sufficient strength and stiffness to puncture tissue. For example, the suture-wire element may include a needle wire section having sufficient columnar strength to be pushed from the first location outside the body (e.g. vascular access from the neck) through a lumen within the first catheter, the abrupt perpendicular turn in the magnetic connection, puncture and cross the tissue between the catheters, enter and travel through the second catheter and exit the body at a second location (e.g. a vascular access at the groin). Once the tip of the needle wire section exits proximal end of the second catheter, the needle wire section can be grasped by the clinician and dragged along with the trailing suture section that is attached to the needle wire section at its proximal end with a junction of sufficient size to pass through all the components through which the needle section passed.

The second section is a string like element or "suture section" that is floppy and is typically slightly longer than the first element, which ensures the folded over portion occurs within the flexible suture material when the ends are aligned and then pulled through both catheters. The suture section is terminated with the implantable tissue anchor (e.g. posterior anchor) at its proximal end, which is mounted within the distal head of the delivery catheter (e.g. GCV delivery catheter), for example, as shown above in FIG. 17. The floppy nature of the suture section is important in facilitating the attachment to the anchor (e.g. wrapping and/or tying), folding flat adjacent to the anchor for delivery, and allowing the section to be cut to length inside the body by conventional cutting tipped catheters, as those depicted between the steps in the FIGS. 16C and 16D, during the procedure. The suture section's length and floppiness also allows the entire suture section to be folded in half, reversing direction, bending at the floppy section proximal of the floppy and stiff junction. This in turn allows the folded portion's placement side by side within a single lumen of the delivery catheter with both the puncturing tip and tissue anchor contained at or near the catheters tip facilitating delivery of the anchor. As the procedure progresses, the folded portion is pulled through the catheter. This configuration leaves the suture section preloaded in the delivery catheter with the most proximal folded suture and needle exposed proximally, with a portion of the needle available to be pushed and advanced from the delivery catheter's proximal end.

In a preferred embodiment, the suture section is longer than the needle wire section such that at least a portion of the suture section remains outside the body during the feeding of the needle wire section through the catheters as described above. In one aspect, the needle is long enough to remain outside the initial vascular entry site (e.g. proximal site) so as to be pushable until the wire section exits the vascular exit site (e.g. distal groin site) so as to be pullable from its distal end. In some embodiments, the needle wire section has a length within a range of 170-200 cm. In the procedure described, in theory, the suture would only need to be long enough to extend from the anchor site to the distal exit. (When the needle wire section exits the groin and is pulled, the suture is doubled over in the delivery catheter and extends to the anchor, such that the distance from the anchor site to the groin would represent the minimal length needed for the suture to exit the body when the needle is pulled entirely through. It is appreciated that in the case of entry through the groin, the distance between the anchor site and the exit site would represent the minimal suture length for the suture to exit the body. However, if the suture section were to become disconnected from the needle wire section before the suture section exits the vascular exit site (e.g. groin site), it would be difficult to retrieve from the body since neither end of the suture section would be outside the body. Thus, it is preferable to use a suture length of sufficient length so that at least a portion of the suture section extends from the proximal site, doubled over in the delivery catheter, and extends all the way to the distal/groin exit site until it is pullable from the distal exit site. Therefore, it is desirable for the suture section to be longer than the required length of the needle section. Preferably, the suture section is of sufficient length so that the suture section extends through both catheters. In some embodiments, the suture section has a length within a range of 180-210 cm. Given the substantial lengths of the suture section and needle wire sections, management of the suture-wire element can be unwieldy and complicated, often requiring multiple people to hold, unwind and help feed the suture-wire through the catheters during a procedure. The suture-wire management devices described herein allow for greatly improved management of such a suture-wire. In some embodiments, the suture-wire management device is integrated within a catheter handle, thereby further improving ease of use and allowing for delivery and deployment of a heart implant by a single clinician.

As described above, the two sections of the suture-wire element must travel through two catheters, exiting at a second vascular access location on the body where tension is then applied to the suture section, and slack is removed to place the anchor with the bridging element (a portion of the suture section) spanning the atrium. After the anchor is placed and catheters removed, the suture section acts as a rail over which other system components are subsequently delivered into the heart with catheters from the second location. Because of these length requirements in this procedure, the length of the suture section far exceeds the length loaded on the initial delivery catheter (e.g. 75-95 cm), even when folded in half. Much of the suture section is exposed proximally and if left unmanaged is available to tangle and interfere with other equipment on the operating table. It desirable to coil or fold and to contain and condense the excess suture section. Simply coiling the folded side-by-side needle wire section and suture section in a tube is not suitable for deployment because the system is deployed sequentially, such that moving the needle section tends to drag the neighboring suture section out of its coil prematurely, causing bunching and tangling. If this configuration is coiled it can also create friction that tends to prevent deployment by locking in a static position, especially when in a compact ergonomic coil configuration. Winding both sections on a rotatable pully or reel is not feasible because unwinding the forward needle wire section automatically and undesirably unwinds the rearward suture section prematurely again causing bunching and tangling of the suture section. Although sequentially winding the system around a peg or sheave is suitable for the suture section, sequential winding is not suitable for the needle section since this section naturally springs outward when wound. Thus, another type of feature, such as an inwardly constraining feature, such as a wall, groove or intermittent clipping system, may be needed. Also, it is desirable to have some counter traction on those proximal most portions of the suture section nearest the anchor within catheter lumen so as to stop the distal portions from dragging adjacent portions distally and possibly tangling or jamming during deployment in the small luminal space. Further, if any intervening element that singularly surrounds one side of the suture or needle were used such a feature would need be readily removable or releasable (e.g. a slit or overlap) to allow the subsequent section to enter the catheter. In the implant delivery and deployment approach described herein, both sections of the side-by-side configuration must enter and exit from the same orifice and luminal space when the system is loaded into the delivery catheter. It is appreciated that this side-by-side switched back configuration cannot rely on conventional technology used by fishing reels, hose reels and other such devices, with the sequential winding on one end over the other and one end terminating separately from the other, because both sections must be together inside a single lumen of the delivery catheter when pulled through from the vascular entry site through the vascular exit site. These aspects can be further understood by referring to the following exemplary embodiments of a suture-wire management devices.

B. Planar Tabbed Device

In one aspect, the suture-wire management device comprises a planar member with features or tabs for engaging the differing sections of the suture-wire element, such as the suture-wire element described above. In some embodiments, the planar member includes a first set of tabs configured and arranged for constraining the earliest deployed, stiffer needle wire section and a second set of tabs configured and arranged for supporting the less stiff suture-wire section when wound thereon.

Figure 20:
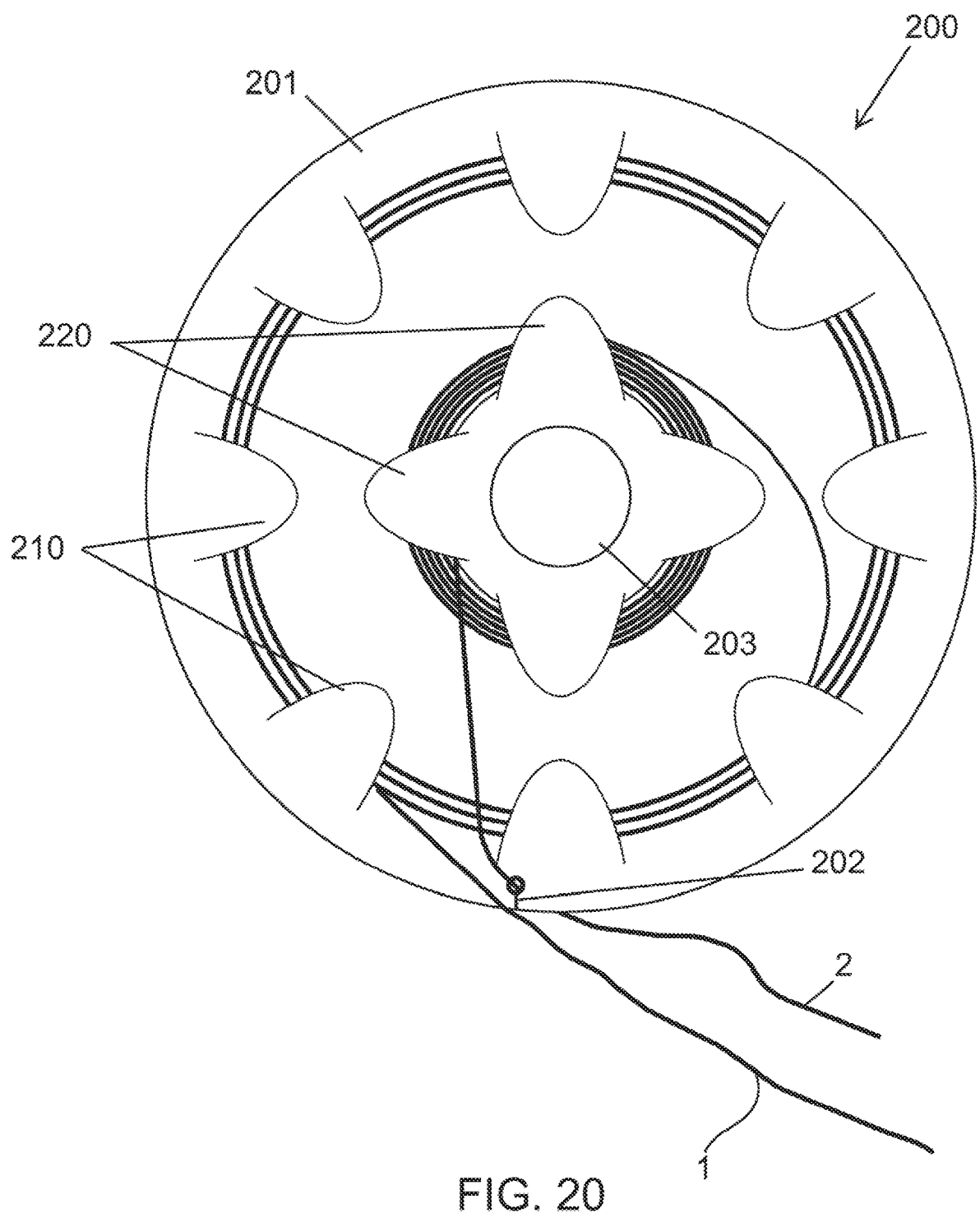
FIG. 20 depicts a planar suture-wire management device, in accordance with some embodiments of the invention.

FIG. 20 shows such an example embodiment, the suture-wire management device 200 defined as an integral planar member 201 with series of features or tabs 210, 220 for engaging sections with differing stiffness. In some embodiments, the device is formed from medical grade plastic or "chip board" card stock with circumferentially punched tabs, a first set of tabs 210 for constraining a stiff wire material and a second set of tabs 220 around which a less stiff suture material can be wound. In this embodiment, the tabs 220 are formed as outwardly facing tabs to sequentially wind and hold the suture section 2 of the bridge and tabs 210 are formed as inwardly facing tabs to sequentially coil and constrain the outwardly pushing needle section of the bridge assembly. This configuration allows for a compact implementation of the device as the wire needle section is more limited than the more flexible suture section as to the most compact coil form possible without unwanted plastic deformation. In other words, the suture section can be wound much smaller than the needle wire section without permanent deformation. This supports the use of super-elastic NiTi wire for the needle section, although any suitable material with sufficient stiffness and strength could be used. In this embodiment having a concentric inner suture/outer needle configuration, it is desirable if the tabs do not interdigitate as to avoid impeding release of the suture-wire element. Spacing the tabs and radially apart allows for free removal of the suture-wire element.

In this embodiment, planar member is defined as a round card 201 with finger/thumb hole 203 at its center allowing the device to be easily held from the underside of the deployment surface of the card as the suture-wire element is dispensed with the other hand above the card. The first set of tabs 210 are formed as a series of inwardly facing tabs that are arranged in an outer circle about the periphery of the round planar card 201 to sequentially coil and constrain the outwardly pushing needle section of the bridge assembly. The second set of tabs 220 are formed as a series of outwardly facing tabs are arranged in a smaller, inner circle to sequentially wind and hold the more flexible suture section 2 of the suture-wire element. In this embodiment, the first and second set of tabs are defined on the same side of the planar card 201. The planar card 201 can further include a slit 202 for securing a portion of the suture section 2 before unwrapping. In some aspects, configurations to avoid tangling of the needle and suture sections, include a side-by-side configuration suture and needle on one side of the card or can include the suture section on one side of the card and needle wire section on the other side. The latter design may include slit to the card edge as an escape for the suture from one card side to the other and or exit or entry to the card. There may be other slits where the bridge enters or exits inner or outer edges of card to capture and stop premature dislodgement of the bridge or to lock the bridge in stable state in any of the above configurations.

C. Disc Enclosure Device

In another aspect, the suture-wire management device is defined as an enclosure that includes differing engagement surfaces within for engaging the differing sections of the suture-wire element. This approach is advantageous in that it secures and improves management of the suture-wire element during advancement through the vasculature pathway, while also protecting and maintaining sterility of the suture-wire within the enclosure. In some embodiments, the enclosure device effectively encases both the excess needle and suture sections, sequentially coiling them inside of a toroidal enclosure. In some embodiments, the enclosure is defined as a tight wound polymeric tube connected end-to-end to form a ring, with the diameter dictated by the tightest plastically undeformed needle wire section coil. The ring can further include a circumferential 360° opening or slit on the top portions of the ring for dispensing the suture-wire. A second radial entry/exit slit on an outer or inner side of the ring is formed generally perpendicular to and emanating from the top of the circumferential slit, terminating near or at the bottom of the ring. When used in the implant procedure described above, the suture section is attached to the mounted anchor (e.g. posterior anchor) and exits the catheter lumen proximally and enters the ring enclosure through the terminus of the entry/exit slit which serves to avoid the turn-by-turn interference of one part of the suture-wire element with the other during dispensing. The rest of the excess suture-wire element, suture section first then needle section is dispensed though the 360° opening inside the ring enclosure with the suture section clinging along the inside groove of the ring enclosure and the needle section pushing naturally to the outside radius or outer groove inside the hollow ring enclosure over the suture section's initial entry point at entry/exit slit. The puncturing tip of the needle wire section is then loaded into the same catheter lumen as the exiting suture. The entry/exit slit allows the loading during manufacture and unloading during the procedure into the circumferential slit, thereby avoiding interference or tangling of the suture at its entry point as they cross at each other along winding and unwinding turns.

Figure 21:
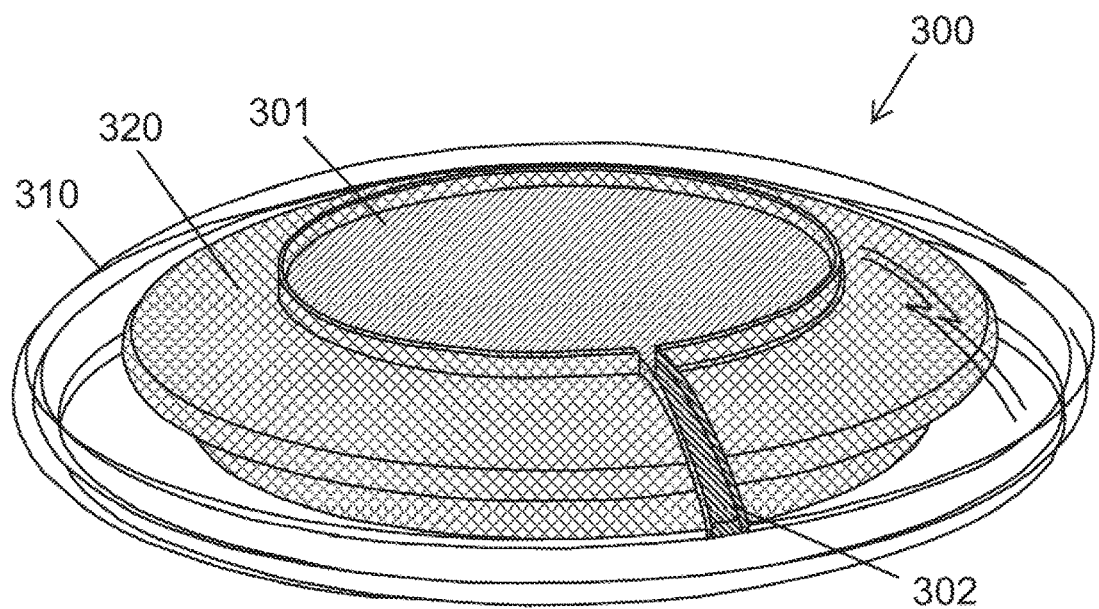
FIGS. 21-22 depicts a ring enclosure suture-wire management device, in accordance with some embodiments of the invention.
Figure 22:
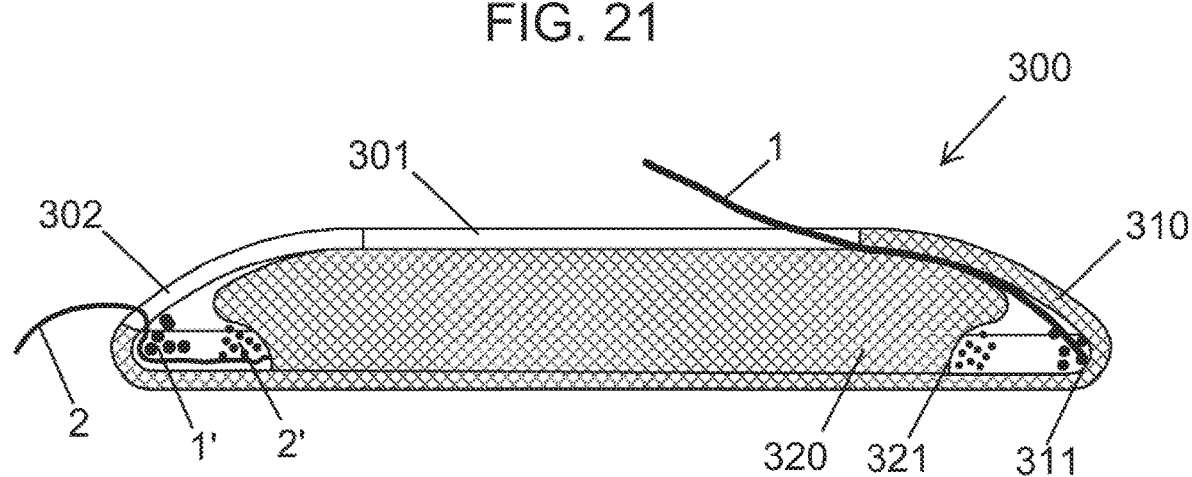

FIGS. 21-22 shows an embodiment the suture-wire device 300 having an outer ring enclosure 310 with a grooved pully like retaining disc 320 disposed within. (Outer ring enclosure 310 is shown as transparent to allow visibility of interior components). Similar to the embodiment described above, the enclosure includes a circumferential 360° slit or opening 301 atop to allow smooth unwinding and dispensing of the sections of the suture-wire element from their respective coils, and a radial entry/exit slit 302 on one side of the outer enclosure 310 that emanates from the top of the circumferential slit and is generally perpendicular thereto for entry/exist of a portion of the suture section. In some embodiments, a compression band or O-ring fits into the slit to further secure the suture section while dispensing the wire needle section through the top circumferential slot 301. As can be seen in the cross-sectional view in FIG. 22, the stiffer wire needle section 1 is secure constrained in a coil 1' by inner facing surface 311 of the outer groove defined by the outer enclosure 310, while the more flexible suture section 2 is wrapped in a coil 2' around outer facing surface 321 of the inner groove defined in the inner disc 302.

In another aspect, the invention pertains to methods of loading a suture-wire element in a suture management device, such as the ring enclosure 300 in FIGS. 21-22, for example, to facilitate use within a delivery system for deployment of an anchor implant, such as any of those described above. The suture-wire element is sequentially wound onto the device 300, suture section then needle section to allow subsequent dispensing of the needle wire section followed by the suture section, as described above. A compression band or O-ring (if used) can then be placed over the wound assembly capturing the suture section and constraining the outward pushing needle. As can be seen in FIG. 22, the suture section 2 extends through the slot 302 and is wound around the inner groove 321, while the wire needle section is wound/constrained within the inner facing surface 311. Notably, a portion of the suture section 2 extends under the wire needle section coil 1' such that the suture-section does not interfere or tangle with the wire needle section when the wire needle section is dispensed. The tip of the wire needle section is fed into the shared lumen of the delivery catheter and during deployment the needle is pushed into the receiving catheter as in other embodiments, with slight resistance provided by band pinching the bridge against the pully at its releasing top edge. The band is notched with a suture entry/exit slit, typically ¼-½, of its width to avoid the turn-by-turn interference of one part of the suture-wire with the other. Alternatively, the suture enters below the band and exits above, and then the band is cut and removed to release the suture-wire during deployment. In some embodiments, the band or O-ring can be replaced by a cap that covers one side (bottom) and the complete edge of the pully. In such a configuration, the cap may be in compression with the pulley to constrain the excess bridge but not necessarily pushing into the grove. The circumferential edge of the cap 311 can be shaped with triangular shaped cross section that is flat on the bottom in the plane of the disc and angled to towards the releasing edge of the cap pulley interface. This configuration stabilizes the outward pushing needle to seek the lowest energy state forcing itself into the triangular corner away from the suture. Like other embodiments, the cap can be notched with a suture entry/exit slit, in this case to from its delivery edge to the inside of the outermost corner. The cap must be sized and be made of a material flexible enough to snapped over the pulley from the bottom D. Integrated Handle Configuration In another aspect, it is desirable for a suture management enclosure device that is integrated with a catheter handle to improve ease of use and further improve handling within a catheter system, preferably to allow a single operator of the catheter to also dispense the suture-wire from the integrated handle. While the previous embodiment can be configured small and light enough to dangle at the end of the catheter held only by the suture bridge itself, such a configuration may still tangle, accidently uncoil and/or interfere with catheter operation. Ideally any of the above embodiments can be integrated into the catheter handle.

Figure 23:
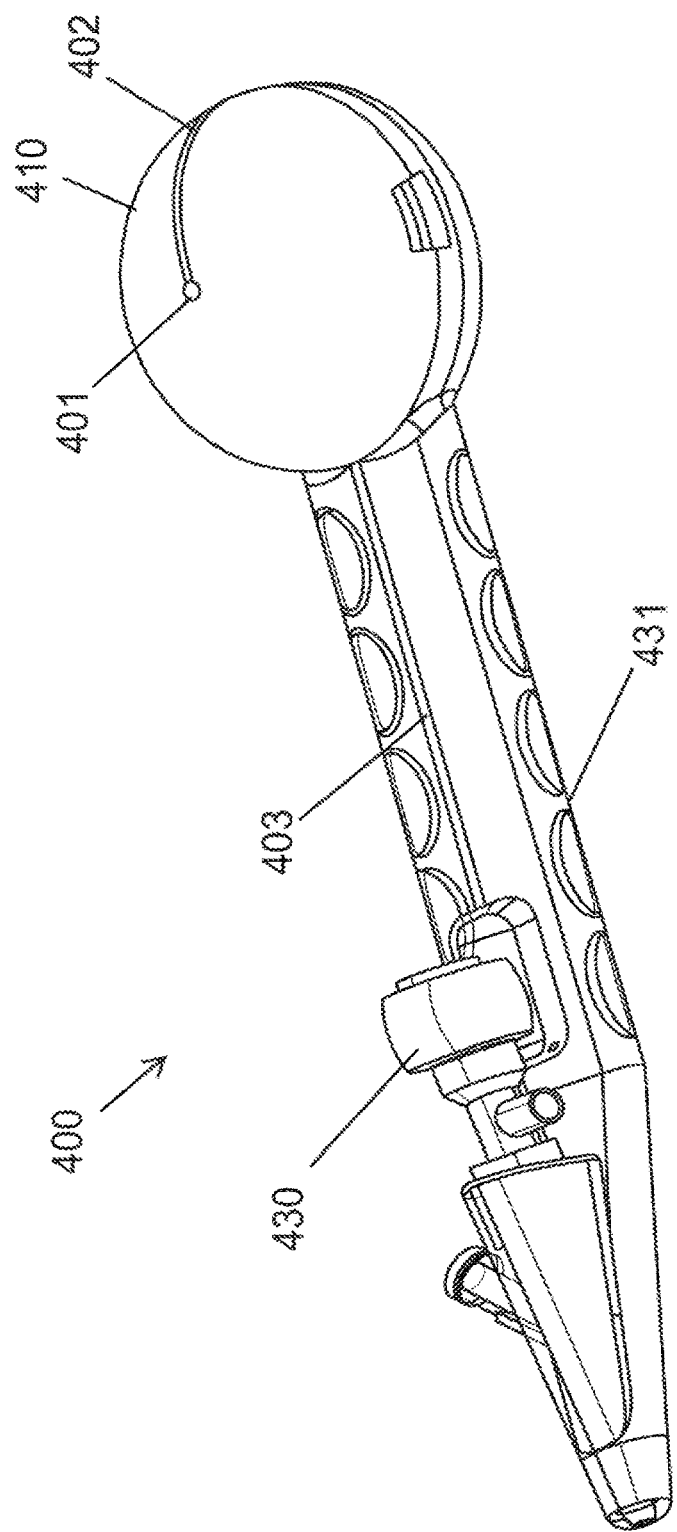
FIGS. 23-24 depicts a delivery catheter handle with integrated suture-wire management device, in accordance with some embodiments of the invention.

FIG. 23 shows an exemplary embodiment of a delivery catheter handle 400 with integrated suture-wire management device. The described handle 400 has two separate components, the handle body 431 and cap 410 that forms an enclosure and protects the coils of the suture-wire element. In this embodiment, the handle and catheter have two lumens, one for the folded suture-wire and one for the guide wire along which the catheter is advanced. This handle may be viewed as having three segments: a distal section that is attached to the flexible catheter shaft at its tip and includes a hemostatic exit port 430 where the folded suture-wire exits proximally; a center section where the operator holds the handle and guides and torques the catheter to its position in the heart or advances the needle wire portion of the suture-wire during deployment, and; a proximal section where the excess suture-wire (needle and suture sections), are coiled and stored under a protective removable cap 410 having a dispensing hole 401 and entry/exit slot 402. Notably, cap 410 rotates such that the side entry/exit slot 402 can be aligned with a center slot 403 within the handle to facilitate loading of the suture-wire and release of the last remaining (switched back) portion of the suture-wire before being pulled entirely through the catheter.

Figure 24:
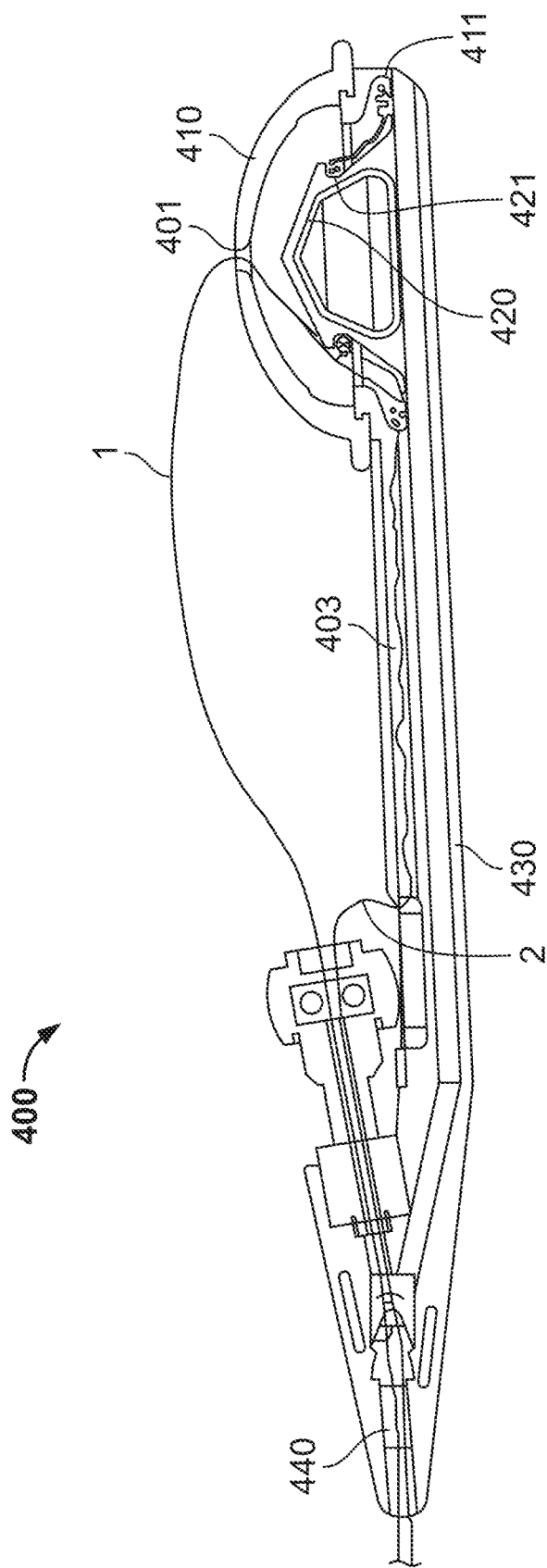

When used in the implant deployment system describe above, the sequence for loading the excess suture-wire element starts with threading the needle section near the distal catheter tip into the magnet exit puncturing side hole then advancing the needle wire section proximally through the bridge lumen until it exits at the hemostatic port 430 in the handle 400. The rest of the suture-wire element is pulled through the catheter, and the anchor is loaded into its retaining portion of the catheter tip and excess slack is removed. As can be seen in FIG. 24, the portion of the suture-wire adjacent to the port is placed in slot 403 in the center section of handle body 431 which leads into the bottom of the proximal section of the handle that holds the coiled suture-wire sections (through slot 402). At the rear of the handle, the suture section of the suture-wire element (one leg) is wound around an inner groove defined under a retaining lip 421 of a conical post until it reaches the needle section of the suture-wire element. The needle section is then loosely wound around the post where it springs into the constraining outer groove 411, which is over the initial leg of suture section that emanates from slot 403 in the handle's center section and extends through slot 402. This position of the needle wire coil on top of a portion of the incoming suture section at the center to rear handle junction facilitates the proper deployment sequence described above by avoiding the turn-by-turn interference of one part of the bridge with the other. The needle tip and length approximately the length of the catheter is fed back into the hemostatic port 430 and advanced to just inside the magnet tip of the delivery catheter, leaving the needle and suture nearest the posterior anchor side-by-side in the bridge lumen of the delivery catheter. The protective cap 410 is then placed over the bridge via the entry/exit slot and snapped into position at the rear of the handle, with the entry/exit slot offset from the slot 403, typically, rotated rearward. Cap 410 serves the purpose of centering the dispensing hole 401 so that the suture-wire dispenses smoothly, without preference for radial alignment around the post, but is not required element for the system to work. The above steps are performed during the manufacturing assembly process of the anchor delivery catheter and not during the deployment procedure.

During the deployment procedure, for example, as shown in FIGS. 14A-16D, the magnetic catheters are positioned in the heart and connected. The operator can then begin the tissue anchor delivery process pushing the system forward, grasping the needle just proximal of the hemostatic port of the handle and advancing it stepwise, inching the system forward until it exits the body at the hub of the second catheter. Note that slot 402 aligns proximally to avoid premature exiting of portions of the suture bridge. The needle wire section 2 is then grasped near its distal tip and pulled. Deploying the needle forward begins unwinding of the needle at rear of the handle through the cap center hole 401 followed seamlessly by suture section 2 until the switched back portion straddles the cap between the center section slot 403 and the cap's exit hole 401, stopping advancement. The cap 410 is then rotated by the operator to align the entry/exit slot 402 distally with the handle slot 403 which releases the switched back suture section from the enclosure and allows the switched back suture section to travel completely through the bridge lumen side by side in the delivery catheter, thereby deploying the anchor on the catheter in the desired position in the heart.

E. Furled Sleeve Device

In another aspect, the suture-wire management device can include a sleeve that encloses the folded suture and includes a retention feature to allow the suture to be gradually withdrawn.

Figure 25:
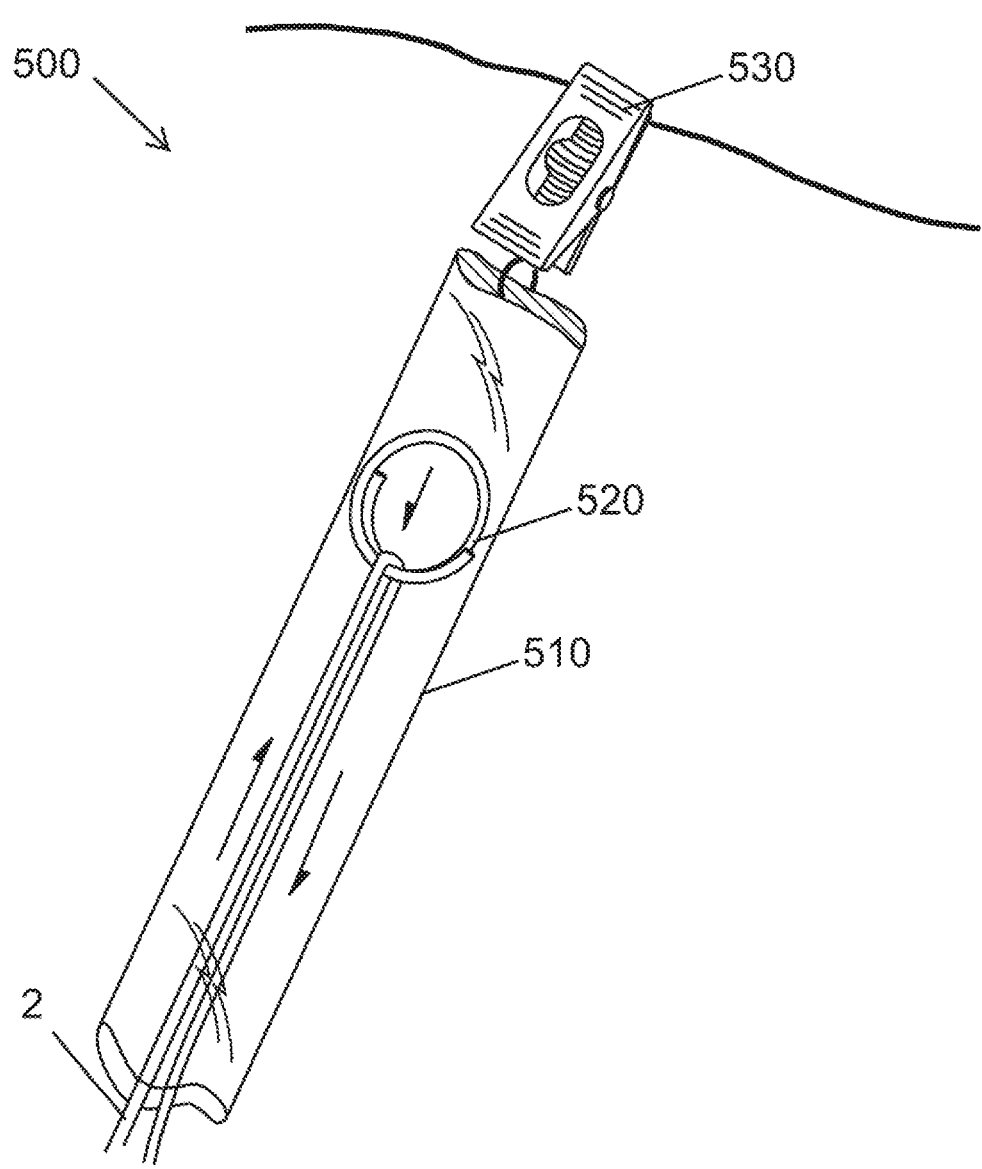
FIGS. 25-26 depicts a sleeve type suture-wire management device, in accordance with some embodiments of the invention.

FIG. 25 shows such an embodiment in which suture-wire management device 500 includes a flattened flexible thin walled sleeve 510 with an inner retention feature 520 that engages a switched-back portion of the suture section of the excess suture-wire to allow for controlled release from the sleeve during the deployment procedure described above. In this embodiment, both sides of the doubled over excess suture section are placed together in the sleeve 510 (shown as transparent for increased visibility of the suture within), the sleeve being slightly longer than the exposed folded suture length. The retention feature 520 is a washer like slit disc with a center hole or overlapping wire or plastic ring (key ring), which is slipped over the folded portion of suture section 2 so that the suture resides inside of the ring 520 at a terminal or switched back portion of the suture 2. The disc or ring retention feature 520 is sized to just under the width of the flattened sleeve 510 or is provided with textural features to create counter traction or drag while sliding in the sleeve 510 as the distal leg of the suture-wire element is advanced, pushed or pulled, through the catheters. This ring element drags against the inside the sleeve 510 while the suture section 2 slides through the center hole pulling the retention feature ring 520 proximal to distal towards the hub of the catheter. The retention ring 520 is removed just prior to last bit of suture section entering the catheter to allow the switched back suture loop to pass through the catheters. The proximal end of the sleeve 510 may terminate in pinching clamp 530 or hook to clasp the table drape or other convenient feature or overhead wire to keep the system aligned and stretched. The sleeve 510 serves the functions of inhibiting the suture-wire bridge element from tangling with itself when packaged before use, inhibiting the suture-wire element from tangling with other implements on the table, and protecting the suture-wire element from contamination as well as the controlled release by the frictional interaction with the dragging ring or similar component described above.

Figure 26:
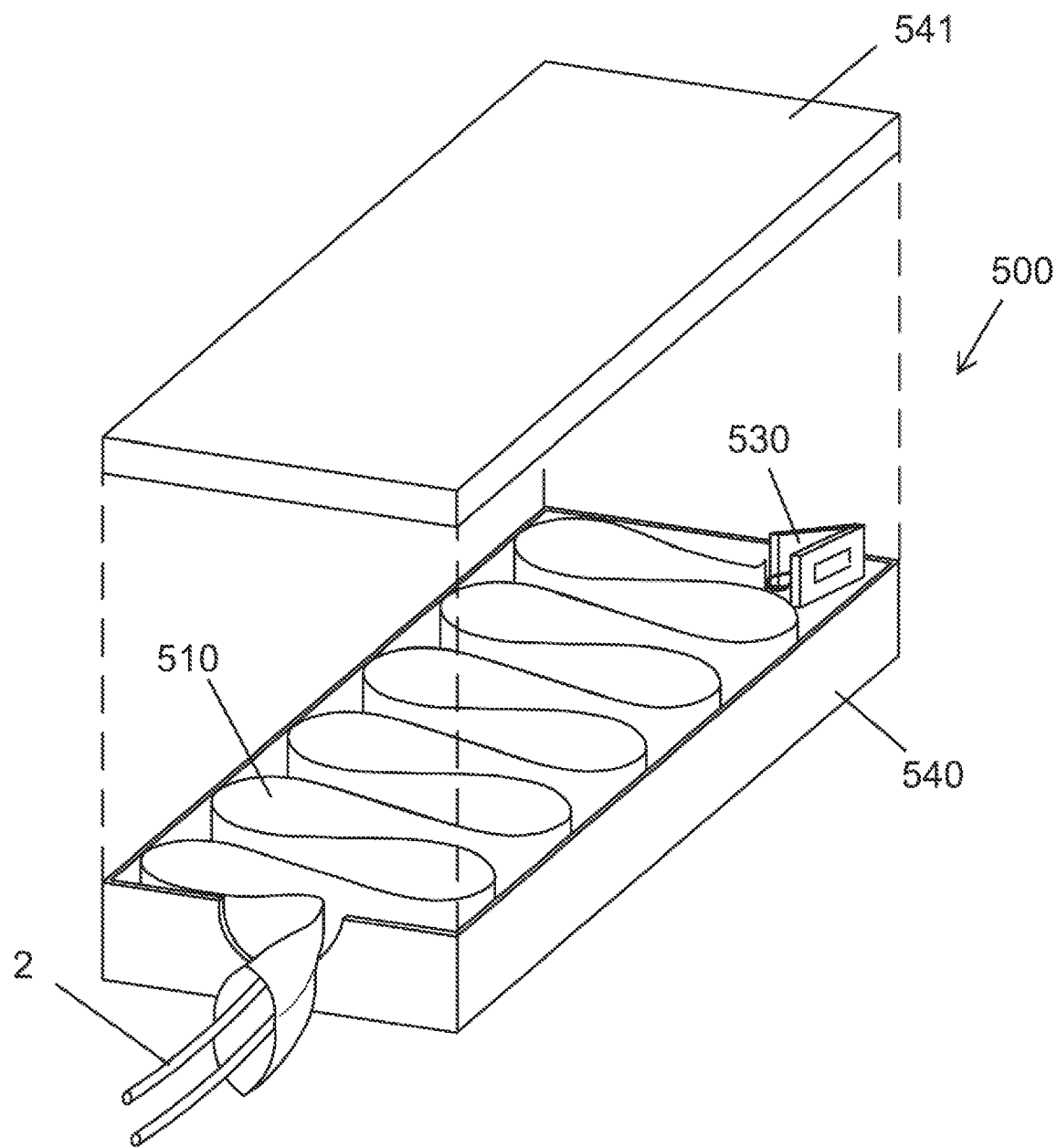

FIG. 26 shows that the entire sleeve device 500 can be flexible enough to be tightly coiled or furled into a protective canister 540 or housing that is part of or separate from the delivery catheter handle to keep the proximal bridge under control until needed for deployment. The canister 540 may have a removable lid 541 or a single orifice to remove and then straighten the assembly on the table when needed.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A catheter handle device with integrated suture-wire management for managing excess suture-wire element, the handle comprising:
    a catheter handle body having a proximal portion and a distal portion;
    a catheter shaft and a hemostatic port provided in the distal portion;
    an enclosure disposed along the proximal portion, the enclosure being configured for storing and managing a loop of excess suture-wire element extending proximally from the hemostatic port, wherein the enclosure includes:
        an inner groove facing radially outward to facilitate winding of a suture section of the suture-wire element thereon within a coil,
        an outer groove facing radially inward to radially constrain a wire section of the suture-wire element in a coil;
        a central opening through which the wire sections and suture sections are sequentially dispensed from their respective coils; and
        a radial slit extending radially from the central opening for passage of a portion of the suture section to avoid interference or tangling when dispensing excess suture-wire element through the central opening.

2. The catheter handle device of claim 1,
    a center portion between the proximal and distal portions, the center portion being configured to facilitate handling of the catheter by an operator.

3. The catheter handle device of claim 1, wherein the enclosure is defined by the proximal portion of the catheter body that interfaces with a releasable cap.

4. The catheter handle device of claim 3, further comprising a conical post disposed within a center of the enclosure, the inner groove being defined by a radially extending upper lip of the conical post.

5. The catheter handle device of claim 3, wherein the outer groove is defined within the proximal portion of the catheter body.

6. The catheter handle device of claim 5, wherein the outer groove is defined as a rounded triangular recess to facilitate sequential coiling of the wire section.

7. The catheter handle device of claim 1, wherein the central opening and the radial slit are provided on a cap of the enclosure.

8. The catheter handle device of claim 7, wherein a center portion of the catheter handle body includes a lengthwise slit extending along the center portion to the proximal portion, wherein the cap is configured to rotate such that the radial slit of the cap aligns with the lengthwise slit of the cap to facilitate release of a last remaining portion of the suture section from the enclosure of the proximal portion.

9. The catheter handle device of claim 8, wherein the cap is rotatable to offset the radial slit from the lengthwise slit of the center portion by 180 degrees.

10. A delivery system for a heart implant for treatment of a heart valve in a heart chamber of a patient, the system comprising:
- a first catheter having a proximal and distal end, wherein the first catheter includes a first lumen extending therethrough for passage of a guidewire, wherein the first catheter further includes:
  - a magnetic head along a distal portion thereof, wherein the magnetic head comprises magnetic poles oriented laterally relative a longitudinal axis of the first catheter and a guide channel defined therein extending to a side hole adjacent a first magnetic pole,
  - a penetrating wire section of a suture-wire element advanceable through a second lumen aligned with the guide channel of the distal magnetic head, wherein the penetrating wire section has a sharpened distal end to facilitate penetration of tissue;
- a posterior anchor releasably coupled with the first catheter along the distal portion thereof;
- a suture section of the suture-wire element, the suture section being configured to act as a bridging element in the implant, wherein the suture section is attached to the posterior anchor at one end and attached to the penetrating wire section at an opposite end such that advancement of the penetrating wire section through the side hole and across the heart chamber facilitates advancement of the suture section across the heart chamber; and
- a suture-wire management device configured for managing excess suture-wire element extending proximally of the first catheter during delivery and deployment of the posterior anchor.

11. The delivery system of claim 10, wherein the suture-wire management device comprises an enclosure for storing and managing excess suture-wire extending from the catheter, wherein the enclosure includes:
- an inner groove facing in a radially outward direction around which the suture section of the excess suture-wire element is coiled, and
- an outer groove surface facing radially inward in which the penetrating wire section of the excess suture-wire element is coiled, the wire section having higher stiffness than the suture section.

12. The delivery system of claim 11, wherein the enclosure of the proximal portion includes a central opening through which the penetrating wire section and the suture section are sequentially dispensed from their respective coils.

13. The delivery system of claim 12, wherein the enclosure further includes a slit emanating from the central opening for passage of a portion of the suture section.

14. The delivery system of claim 11, wherein the inner groove is defined by a conical post within a center of the enclosure and a radially extending upper lip of the conical post.

15. The delivery system of claim 11, wherein the outer groove is defined within an outer housing of the enclosure.

16. The delivery system of claim 15, wherein the outer groove has a rounded triangular contour to facilitate sequential coiling of the penetrating wire section.

17. The delivery system of claim 11, wherein the suture-wire management device is integrated within a catheter handle attachable to the first delivery catheter.

18. The delivery system of claim 17, wherein the catheter handle comprises:
- a catheter handle body having a proximal portion, a center portion and a distal portion, the distal portion having a flexible catheter shaft and a hemostatic exit port, the center portion being configured to facilitate handling of the catheter by an operator, and the proximal portion including the enclosure.

19. The delivery system of claim 10, further comprising:
- a second catheter having a proximal and distal end, wherein the second catheter includes a first lumen extending therethrough for passage of a guidewire, wherein the second catheter further includes:
  - a second magnetic head along a distal portion thereof, wherein distal the second magnetic head comprises magnetic poles oriented axially relative a longitudinal axis of the second catheter and an axial channel defined therein extending to a distal hole adjacent a first magnetic pole.

20. The delivery system of claim 19, wherein the penetrating wire section has a length greater than the total length of the first lumen and a second lumen of the second catheter so as to allow manual advancement of the penetrating wire section externally from a first vascular access point associated with the first catheter until the penetrating wire extends through the second lumen of the second catheter externally of a second vascular access point associated with the second catheter.

21. The delivery system of claim 20, wherein the suture section has a length greater than a length of the penetrating wire section so that at least a portion remains outside of a body of the patient as the suture section is drawn through the first and second catheters.

22. A device for managing a suture-wire element having a suture section and a needle wire section of increased stiffness, the device comprising:
- a housing having a generally rounded shape along a major plane thereof and defining an enclosure;
- an inner groove surface defined within the enclosure, the inner groove facing in a radially outward direction and configured for winding of the suture section thereon within a coil;
- an outer groove surface defined within the enclosure and facing radially inward and configured for constraining a coil of the wire section therein;
- a circular opening along an upper surface of the housing when the major plane is horizontal for a sequential dispensing of the suture section and the wire section therethrough from within the enclosure; and
- a slit extending radially from the circular opening for passage of a portion of the suture section to avoid interference or tangling when dispensing excess suture-wire element through the circular opening.

23. The device of claim 22, wherein the slit extends at least partly along one side of the housing.

24. The device of claim 22 further comprising:
a compression band or O-ring fits dimensioned and configured to further secure the suture section coil while dispensing the wire needle section through the opening.

25. A method of loading a suture wire element having a suture section and a wire section of increased stiffness in a suture-wire management device, the method comprising:
placing the suture section within the device such that a portion of the suture section extends into an enclosure of the device or is secured onto the device;
winding the suture section about an inner winding surface of the device within a first coil; and
after winding the suture section, winding the wire section of increased stiffness about an outer winding surface of the device that constrains the needle wire section within a second coil having a larger diameter than the first coil,
wherein the portion of the suture section extends under the second coil of the needle wire coil so as to facilitate dispensing of the needle wire section from the second coil before dispensing of the suture section from the first coil.

* * * * *